US010301647B2

(12) United States Patent
Lee et al.

(10) Patent No.: US 10,301,647 B2
(45) Date of Patent: May 28, 2019

(54) ADENOVIRAL-BASED BIOLOGICAL DELIVERY AND EXPRESSION SYSTEM FOR USE IN THE TREATMENT OF OSTEOARTHRITIS

(71) Applicant: Baylor College of Medicine, Houston, TX (US)

(72) Inventors: Brendan Lee, Houston, TX (US); Kilian Guse, Helsinki (FI); Zhechao Ruan, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 14/375,351

(22) PCT Filed: Jan. 23, 2013

(86) PCT No.: PCT/IB2013/000198

§ 371 (c)(1),
(2) Date: Jul. 29, 2014

(87) PCT Pub. No.: WO2013/114199

PCT Pub. Date: Aug. 8, 2013

(65) Prior Publication Data

US 2015/0031083 A1 Jan. 29, 2015

(30) Foreign Application Priority Data

Feb. 2, 2012 (EP) .................................... 12000703

(51) Int. Cl.

| | |
|---|---|
| ***C12N 15/861*** | (2006.01) |
| ***A61K 48/00*** | (2006.01) |
| ***C07K 14/545*** | (2006.01) |
| ***C12N 15/86*** | (2006.01) |
| ***C12N 7/00*** | (2006.01) |

(52) U.S. Cl.

CPC ............ *C12N 15/86* (2013.01); *C07K 14/545* (2013.01); *C12N 7/00* (2013.01); *A61K 48/00* (2013.01); *C12N 2710/10043* (2013.01); *C12N 2710/10071* (2013.01); *C12N 2710/10343* (2013.01); *C12N 2710/10371* (2013.01); *C12N 2800/24* (2013.01)

(58) Field of Classification Search

None

See application file for complete search history.

(56) References Cited

U.S. PATENT DOCUMENTS

| | | | | |
|---|---|---|---|---|
| 5,747,072 | A | 5/1998 | Davidson et al. | |
| 2002/0081719 | A1* | 6/2002 | Massaad .............. | C07K 14/705 435/320.1 |
| 2003/0091536 | A1 | 5/2003 | Frisbee et al. | |
| 2012/0045764 | A1* | 2/2012 | Grompe ............. | A01K 67/0271 435/6.11 |

FOREIGN PATENT DOCUMENTS

WO WO 02/082908 A1 10/2002

OTHER PUBLICATIONS

Vetrini et al, Gene Therapy with Helper-Dependent Adenoviral Vectors: Current Advances and Future Perspectives, Viruses 2010, 2, 1886-1917.*

Bakker et al, C3-Tat/HIV-Regulated Intraarticular Human Interleukin-1 Receptor Antagonist Gene Therapy Results in Efficient Inhibition of Collagen-Induced Arthritis Superior to Cytomegalovirus-Regulated Expression of the Same Transgene, Arthritis & Rheumatism vol. 46, No. 6, Jun. 2002, pp. 1661-1670.*

Ross et al, Host Cell Detection of Noncoding Stuffer DNA Contained in Helper-Dependent Adenovirus Vectors Leads to Epigenetic Repression of Transgene Expression. Journal of Virology, Sep. 2009, p. 8409-8417.*

Daya et al, Gene Therapy Using Adeno-Associated Virus Vectors, Clin. Microbiol. Rev, 2008, 21(4), pp. 583-593.*

Fumoto et al, Targeted Gene Delivery: Importance of Administration Routes, Chapter 1, Intech, 2013, pp. 3-31.*

Frisbie et al, Treatment of experimental equine osteoarthritis by in vivo delivery of the equine interleukin-1 receptor antagonist gene, Gene Therapy (2002) 9, 12-20.*

Chen et al, Effects of adenovirus-mediated bFGF, IL-1Ra and IGF-1 gene transfer on human osteoarthritic chondrocytes and osteoarthritis in rabbits, Experimental and Molecular Medicine, vol. 42, No. 10, 684-695, Oct. 2010.*

Vetrini and Ng, Gene Therapy with Helper-Dependent Adenoviral Vectors: Current Advances and Future Perspectives. Viruses 2010, 2, 1886-1917.*

Bakker, A. et al, "C3-Tat/HIV-regulated intraarticular human interleukin-1 receptor antagonist gene therapy results in efficient inhibition of collagen-induced arthritis superior to cytomegalovirus-regulated expression of the same transgene.", Arthritis and Rheumatism, 46:6:1661-1670, XP002675514, (Jun. 2002).

Palmer, D. et al, "Improved system for helper-dependent adenoviral vector production", Molecular Therapy: The Journal of the American Society of Gene Therapy, 8:5:846-852, XP002675515, (Nov. 2003).

(Continued)

*Primary Examiner* — Maria Marvich

(74) *Attorney, Agent, or Firm* — Cooley LLP; Ivor R. Elrifi; Christina K. Stock

(57) ABSTRACT

The invention relates to an adenoviral-based biological delivery and expression system for use in the treatment or prevention of osteoarthritis in human or mammalian joints by long-term inducible gene expression of human or mammalian interleukin-1 receptor antagonist (Il-1Ra) in synovial cells, comprising a helper-dependent adenoviral vector containing a nucleic acid sequence encoding for human or mammalian interleukin-1 receptor antagonist (Il-1Ra), left and right inverted terminal repeats (L ITR and R ITR), the adenoviral packaging signal and non-viral, non-coding stuffer nucleic acid sequences, wherein the expression of the human or mammalian interleukin-1 receptor antagonist (Il-1Ra) gene within synovial cells is regulated by an inflammation-inducible promoter.

7 Claims, 6 Drawing Sheets

Specification includes a Sequence Listing.

(56) References Cited

OTHER PUBLICATIONS

Toietta, G. et al, "Generation of helper-dependent adenoviral vectors by homologous recombination", Molecular Therapy: The Journal of the American Society of Gene Therapy, 5:2:204-210, XP002675516, (Feb. 2002).
Khoury, M., "Inflammation-inducible anti-TNF gene expression mediated by intra-articular injection of serotype 5 adeno-associated virus reduces arthritis", The Journal of Science Medicine, 9:7:596-604, XP002675517, (Jul. 2007).
Caron, J. et al, "Chondroprotective effect of inrtaarticular injections of interlukin-1 receptor antagonist in experimental osteoarthritis. Supression of collagenase-1 expression.", Arthritis Rheumatism, 39:9:1535-1544, (Sep. 1996).
Dinarello, C., "The Cytokine Handb000k", 4th Edition, Chapter 27—Interlukin-1 family, vol. 2, pp. 643-668, (2003).
Evans, C. et al, "Gene therapy for arthritis", Gene Therapeutics: Methods and Applications of direct Gene Transferm, Birkhauser: Boston, MA, pp. 320-343, (1994).
Parks, R., "Improvements in adenoviral vector technology: overcoming barriers for gene therapy", Clinical Genetics, vol. 58, pp. 1-11, (2000).
Brunetti-Pierri, R. et al, "Multi-Year Transgene expression in nonhuman primates following Hepatic transduction with helper-dependent adenoviral vectors", American Society of Gene & Cell Therapy, Annual meeting 2011 molecular therapy, vol. 19, Supp. 1, (May 2011).
Mitani, K. et al, "Rescue, propagation, and partial purification of a helper virus-dependent adenovirus vector", Proc. Natl. Acad. Sci. USA, vol. 92, pp. 3854-3858, (Apr. 1995).
Parks, R. et al, "A helper-dependent adenovirus vector system: Removal of helper virus by Cre-mediated excision of the viral packaging signal", Proc. Natl. Acad. Sci. USA, vol. 92, pp. 13565-13570, (Nov. 1996).
Evans, C. et al, "Osteoarthritis gene therapy", Gene Therapy, Nature Publishing Group, vol. 11, pp. 379-389, (2004).
Suzuki, M. et al, "Large-Scale Production of High-Quality Helper-Dependent adenoviral vectors using adherent cells in call factories", Human Gene Therapy, PMCID: PMC2829450, 21:1:120-128, (Jan. 2010).
Ruan, M. et al, "Quantitative imaging of murine osteoarthritic cartilage by phase contrast micro-computed tomography", Arthritis Rheumatism, 65:2:388-396, Baylor College, Houston, TX, doi: 10.1002/art.37766, (Feb. 2013).
Frisbee, D. et al, "Treatment of experimental equine osteoarthritis by in vivo delivery of the equine interlukin-1 receptor antagonist gene", Gene Therapy, Nature Publishing Group, vol. 9, pp. 12-20, (2002).
Hunter, D. et al, "Emerging drugs for osteoarthritis", Expert Opinon Emerg Drugs, 16:3:479-491, doi: 10.1517/14728214.2011.576670, (Sep. 2011).
Caron, J. et al, "Principals and practices of joint disease treatment", In: Diagnosis and management of lameness in the horse, 1st Edition, Philadelphia: Saunders, pp. 746-764, (2003).
Matthews, G. et al, "Emerging drugs for osteoarthritis", Expert Opinion Emerging Drugs, pp. 1-13, (2011).
Brooks, P., "Impact of osteoarthritis on individuals and society : how much disability? Social consequences and health economic implications.", Current Opinon Rheumatol, vol. 14, pp. 573-577, ((2002).
Accession No. NM_001082525.2 "Equus caballus interleukin 1 receptor antagonist (IL1RN), mRNA", 2015, 3 pages.
Accession No. NM_001082770 "Oryctolagus cuniculus interleukin 1 receptor antagonist (ILIRN, mRNA" 2011, 2 pages.
Accession No. NM_174357.3, "Bos taurus interleukin 1 receptor antagonist (IL1RN), mRNA", 2009, 2 pages.
Bakker et al. "A tropism-modified adenoviral vector increased the effectiveness of gene therapy for arthritis", Gene Therapy, vol. 8, No. 23, p. 1785-1793 (2001).
Bergelson et al. "Isolation of a Common Receptor for Coxsackie B Viruses and Adenoviruses 2 and 5", Science, vol. 275, p. 1320-1323 (1997).
Brunetti-Pierri, R. et al. "Acute Toxicity After High-Dose Systemic Injection of Helper-Dependent Adenoviral Vectors into Nonhuman Primates", Human Gene Therapy, vol. 15, p. 35-46 (2004).
Goodrich et al. "Direct adenovirus-mediated IGF-I gene transduction of synovium induces persisting synovial fluid IGF-I ligand elevations", Gene Therapy, vol. 13, p. 1253-1262 (2006).
Goodrich et al. "Ex Vivo Serotype-Specific Transduction of Equine Joint Tissue by Self-Complementary Adeno-Associated Viral Vectors", Human Gene Therapy, vol. 20, p. 1697-1702 (2009).
Goodrich et al. "Optimization of scAAVIL-lra In Vitro and In Vivo to Deliver High Levels of Therapeutic Protein for Treatment of Osteoarthritis", Molecular Therapy Nucleic Acids, vol. 5, No. 2, e70, 10 pages (2013).
Goodrich et al. "scAAVIL-lra dosing trial in a large animal model and validation of long-term expression with repeat administration for osteoarthritis therapy", Gene Therapy, vol. 22, No. 7, p. 536-545 (2015).
Goossens et al. "Infection Efficiency of Type 5 Adenoviral Vectors in Synovial Tissue Can Be Enhanced With a Type 16 Fiber", Arthritis & Rheumatism, vol. 44, No. 3, p. 570-577, (2001).
Goossens et al. "The Influence of Synovial Fluid on Adenovirus-Mediated Gene Transfer to the Synovial Tissue", Arthritis & Rheumatism, vol. 44, No. 1, p. 48-52 (2001).
Ishihara et al. "Inflammation and Immune Response of Intra-Articular Serotype 2 Adeno-Associated Virus or Adenovirus Vectors in a Large Animal Model", Arthritis, vol. 2012, Article ID: 735472, 8 pages, (2012).
Mingozzi et al., "CD8+ T-cell responses to adenoassociated virus capsid in humans", Nature Medicine, vol. 13, No. 4, p. 419-422 (2007).
Morral et al. "Lethal Toxicity, Severe Endothelial Injury, and a Threshold Effect with High Doses of an Adenoviral Vector in Baboons", Human Gene Therapy, vol. 13, p. 143-154 (2002).
Muruve et al. "Helper-Dependent Adenovirus Vectors Elicit Intact Innate but Attenuated Adaptive Host Immune Responses In Vivo", Journal of Virology, vol. 78, No. 11, p. 5966-5972 (2004).
NCT00617032 "Phase 1 Dose Escalation Study of Intra-Articular Administration of tgAAC94", 8 pages, 2008.
NCT00126724 "Study of Intra-articular Delivery of tgAAC94 in Inflammatory Arthritis Subjects", 11 pages, 2005.
NCT02790723 "Safety of Intra-Articular Sc-rAAV2.51L-1Ra in Subjects With Moderate Knee Oa (AAVIL-1Ra)", 2016.
Ruan et al. "Proteoglycan 4 Expression Protects Against the Development of Osteoarthritis", Science Translational Medicine, vol. 5, No. 176, p. 176ra34, 26 pages, (2013).
Santangelo et al. "Detectable Reporter Gene Expression following Transduction of Adenovirus and Adeno-Associated Virus Serotype 2 Vectors within Full-Thickness Osteoarthritic and Unaffected Canine Cartilage In Vitro and Unaffected Guinea Pig Cartilage In Vivo", Journal of Orthopedic Research, vol. 28, No. 2, p. 149-155, (2010).
Toh et al "Enhancement of Adenovirus-Mediated Gene Delivery to Rheumatoid Arthritis Synoviocytes and Synovium by Fiber Modifications: Role of Arginine-Glycine-Aspartic Acid (RGD)-and Non-RGD-Binding Integrins", Journal of Immunology, vol. 175, No. 11, p. 7687-7698 (2005).
Ulrich-Vintner et al. "In vivo gene delivery to articular chondrocytes mediated by an adeno-associated virus vector", Journal of Orthopedic Research, vol. 22, p. 726-34 (2004).
White et al. "Gene therapy for hemophilia A", Textbook of Hemophilia, Chapter 39, 4 pages, (2007).
Willet et al. "Immunology of AAV-mediated gene transfer in the eye", Frontiers in Immunology, vol. 4, Article 261, 8 pages, (2013).
Flexion Press Release, "Flexion Therapeutics Announces Presentation of Positive FX201 Data at the Osteoarthritis Research Society International World Congress," (Apr. 29, 2018), 2 pages.
Grol et al., "Interleukin-1 Receptor Antagonist Gene Therapy Prevents and Delays Surgically-Induced Osteoarthritis in Small and Large Animal Models," 2018 World Congress of Osteoarthritis (Apr. 26-29, 2018), 26 pages.

(56) References Cited

OTHER PUBLICATIONS

Palmer and Ng, "Helper-Dependent Adenoviral Vectors for Gene Therapy," Human Gene Therapy, vol. 16, (2005), p. 1-16.
Suzuki et al., "MyD88-Dependent Silencing of Transgene Expression During the Innate and Adaptive Immune Response to Helper-Dependent Adenovirus," Human Gene Therapy, vol. 21, (2010), p. 325-336.

* cited by examiner

SEQUENCE LISTING

<160> NUMBER OF SEQ ID NOS: 3

<210> SEQ ID NO 1
<211> LENGTH: 535
<212> TYPE: DNA
<213> ORGANISM: Artificial sequence
<220> FEATURE:
<223> OTHER INFORMATION: /note="Description of Artificial sequence: murine Il1-Ra"
<220> FEATURE:
<221> NAME/KEY: source
<222> LOCATION: (1)..(535)
<223> OTHER INFORMATION: /note="Description of Artificial sequence: murine Il1-Ra"
<220> FEATURE:
<221> NAME/KEY: source
<222> LOCATION: (1)..(535)

<400> SEQUENCE: 1
atggaaatct gctggggacc ctacagtcac ctaatctctc tccttctcat ccttctgttt 60
cattcagagg cagcctgccg cccttctggg aaaagaccct gcaagatgca agccttcaga 120
atctgggata ctaaccagaa gaccttttac ctgagaaaca accagctcat tgctgggtac 180
ttacaaggac caaatatcaa actagaagaa aagatagaca tggtgcctat tgaccttcat 240
agtgtgttct tgggcatcca cgggggcaag ctgtgcctgt cttgtgccaa gtctggagat 300
gatatcaagc tccagctgga ggaagttaac atcactgatc tgagcaagaa caaagaagaa 360
gacaagcgct ttaccttcat ccgctctgag aaaggcccca ccaccagctt tgagtcagct 420
gcctgtccag gatggttcct ctgcacaaca ctagaggctg accgtcctgt gagcctcacc 480
aacacaccgg aagagcccct tatagtcacg aagttctact tccaggaaga ccaat 535

<210> SEQ ID NO 2
<211> LENGTH: 29612
<212> TYPE: DNA
<213> ORGANISM: Artificial sequence
<220> FEATURE:
<223> OTHER INFORMATION: /note="Description of Artificial sequence: Murine helper-dependent adenovirus-Il1-Ra"
<220> FEATURE:
<221> NAME/KEY: source
<222> LOCATION: (1)..(29612)
<223> OTHER INFORMATION: /note="Description of Artificial sequence: Murine helper-dependent adenovirus-Il1-Ra"
<220> FEATURE:
<221> NAME/KEY: source
<222> LOCATION: (1)..(29612)

<400> SEQUENCE: 2
aaacatcatc aataatatac cttattttgg attgaagcca atatgataat gagggggtgg 60
agtttgtgac gtggcgcggg gcgtgggaac ggggcgggtg acgtagtagt gtggcggaag 120
tgtgatgttg caagtgtggc ggaacacatg taagcgacgg atgtggcaaa agtgacgttt 180
ttggtgtgcg ccggtgtaca caggaagtga caattttcgc gcggttttag gcggatgttg 240
tagtaaattt gggcgtaacc gagtaagatt tggccatttt cgcgggaaaa ctgaataaga 300
ggaagtgaaa tctgaataat tttgtgttac tcatagcgcg taatatttgt ctagggccgc 360
ggggactttg accgtttacg tggagactcg cccaggtgtt tttctcaggt gttttccgcg 420

-continued

```
ttccgggtca aagttggcgt tttgatatca agcttatcga taccgtaaac aagtctttaa    480
ttcaagcaag actttaacaa gttaaaagga gcttatgggt aggaagtagt gttatgatgt    540
atgggcataa agggttttaa tgggatagtg aaaatgtcta taataatact taaatggctg    600
cccaatcacc tacaggattg atgtaaacat ggaaaaggtc aaaaacttgg gtcactaaaa    660
tagatgatta atggagagga tgaggttgat agttaaatgt agataagtgg tcttattctc    720
aataaaaatg tgaacataag gcgagtttct acaaagatgg acaggactca ttcatgaaac    780
agcaaaaact ggacatttgt tctaatcttt gaagagtatg aaaaattcct attttaaagg    840
taaaacagta actcacagga aataccaacc caacataaaa tcagaaacaa tagtctaaag    900
taataaaaat caaacgtttg cacgatcaaa ttatgaatga aattcactac taaaattcac    960
actgattttg tttcatccac agtgtcaatg ttgtgatgca tttcaattgt gtgacacagg   1020
cagactgtgg atcaaaagtg gtttctggtg cgacttactc tcttgagtat acctgcagtc   1080
ccctttctta agtgtgttaa aaaaaaaggg ggatttcttc aattcgccaa tactctagct   1140
ctccatgtgc tttctaggaa acaagtgtta acccacctta tttgtcaaac ctagctccaa   1200
aggacttttg actccccaca aaccgatgta gctcaagaga gggtatctgt caccagtatg   1260
tatagtgaaa aaagtatccc aagtcccaac agcaattcct aaaaggagtt tatttaaaaa   1320
accacacaca cctgtaaaat aagtatatat cctccaaggt gactagtttt aaaaaaacag   1380
tattggcttt gatgtaaagt actagtgaat atgttagaaa aatctcactg taaccaagtg   1440
aaatgaaagc aagtatggtt tgcagagatt caaagaaaat ataagaaaac ctactgttgc   1500
cactaaaaag aatcatatat taaatatact cacacaatag ctcttcagtc tgataaaatc   1560
tacagtcata ggaatggatc tatcactatt tctattcagt gctttgatgt aatccagcag   1620
gtcagcaaag aatttatagc ccccccttgag cacacagagg gctacaatgt gatggcctcc   1680
catctccttc atcacatctc gagcaagacg ttcagtccta cagaaataaa atcaggaatt   1740
taatagaaag tttcatacat taaactttat aacaaacacc tcttagtcat taaacttcca   1800
caccaacctg ggcaatatag tgagacccca tgcctgcaaa aaaaaaaaaa ttagccaggc   1860
atggtagcat gtacctgtag tcccagctac ttgagaggtg aggtgggaaa atcactttag   1920
tgcaggatgt tgaggctgga gtgaactgtg attgtgccac tgcactccag cctggacaat   1980
agagcaagac cttgtctcaa aaaaatgcat taaaaatttt ttttaaatct tccacgtatc   2040
acatcctttg ccctcatgtt tcataaggta aaaaatttga taccttcaaa aaaaccaagc   2100
ataccactat cataattttt tttaaatgca aataaaaaca agataccatt ttcacctatc   2160
agactggcag gttctgatta aatgaaattt tctggataat atacaatatt aagagagact   2220
gtagaaactg ggccagtggc tcatgcctgt aatcccagca ctttgggagg ctgggtaaca   2280
tggcgaaccc tgtttctaca aaataaaaat attagctggg agtggtggcg cacacctata   2340
gtcccagcta ctcaggaggc tgaggtggaa ggatcgcttg aacccaggag gttgagactg   2400
cagtgaactg tgatcattct gctgcactgc accccagcct gggcaacaga gaccttgtct   2460
caaaaaaaaa aaaaaaagag acaaattgtg aagagaaagg tactctcata taacatcagg   2520
agtataaaat gattcaactt cttagaggaa aatttggcaa taccaaaata ttcaataaac   2580
tctttcccct tgacccagaa attccacttg aataaagctg aacaagtacc aaacatgtaa   2640
aagaatgttt cttctagtac agtcggtaag aacaaaatag tgtctatcaa tagtggactg   2700
gttaaatcag ttatggtatc tccataagac agaatgctat gcaaccttta aaatatatta   2760
gatagctcta gacacactaa tattaaaagt gtccaataac atttaaaact atactcatac   2820
```

```
gttaaaatat aaatgtatat atgtactttt gcatatagta tacatgcata ggccagtgct   2880
tgagaagaaa tgtgtacaga aggctgaaag gagagaactt tagtcttctt gtttatggcc   2940
tccatagtta gaatatttta taacacaaat attttgatat tataatttta aaataaaaac   3000
acagaatagc cagacataca atgcaagcat tcaataccag gtaaggtttt tcactgtaat   3060
tgacttaaca gaaaattttc aagctagatg tgcataataa taaaaatctg accttgcctt   3120
catgtgattc agccccagtc cattaccctg tttaggactg agaaatgcaa gactctggct   3180
agagttcctt cttccatctc ccttcaatgt ttactttgtt ctggtcccta cagagtccca   3240
ctataccaca actgatacta agtaattagt aaggccctcc tcttttattt ttaataaaga   3300
agattttaga aagcatcagt tatttaataa gttggcctag tttatgttca aatagcaagt   3360
actcagaaca gctgctgatg tttgaaatta acacaagaaa aagtaaaaaa cctcatttta   3420
agatcttact tacctgtcca taattagtcc atgaggaata aacacccttt ccaaatcctc   3480
agcataatga ttaggtatgc aaaataaatc aaggtcataa cctggttcat catcactaat   3540
ctgaaaaaga aatatagctg tttcaatgag agcattacag gatacaaaca tttgattgga   3600
ttaagatgtt aaaaaataac cttagtctat cagagaaatt taggtgtaag atgatattag   3660
taactgttaa ctttgtaggt atgataatga attatgtaag aaaacaacag gccgggcggg   3720
ttggttcaca cgtgtaatcc cagcactttg ggaggctgag gcaggcagac tgcctgagct   3780
caggagttcg agaccagcct gggcaacacg gtgaaatccc gtctctacta aaaatacaaa   3840
aaaattagcc gggtgtggtg acacatgcct gtagtcccag ctacttggga ggctgaggca   3900
ggagaatcac ttgaacctgg gaggtgaagg ttgcagtgag ccaagatggc accacttcac   3960
tccagcctgg gaaacagagc aagactctgt ctctgagctg agatggcacc acttcactcc   4020
agcctgggaa acagagcaag actctgtctc aaaaaaaaca aaacacacaa acaaaaaaac   4080
aggctgggcg cggtggctca cgcctgtaat cccagcactt tgggaggccg aggcgggtgg   4140
atcacctgag gtcaggagtt ccagaccagc cttgtcaaca tggtgaaacc tccccccgcc   4200
gtctctacta aaaatacaaa aattagccag gcgtggtggc aggagcctgt aatcccagct   4260
acttgggagg ctgaggcagg agaatcgctt gtacccagaa ggcagaggtt gcactgagct   4320
gagatggcac cattgcactc cagcctgggg gacaagagcg agatttcgtc tttaaaaaac   4380
aaaaacaaaa caaaaaacca tgtaactata tgtcttagtc atcttagtca agaatgtaga   4440
agtaaagtga taagatatgg aatttccttt aggtcacaaa gagaaaaaga aaaattttaa   4500
agagctaaga caaacgcagc aaaatcttta tatttaataa tattctaaac atgggtgatg   4560
aacatacggg tattcattat actattctct ccacttttga gtatgtttga aaatttagta   4620
aaacaagttt taacacactg tagtctaaca agataaaata tcacactgaa caggaaaaac   4680
tggcatggtg tggtggctca cacttgtaat cccagtgctt tgggaggctg agacaggaga   4740
gttgcttgag gccaggagtt caagaccgac atggggaatg tagcaagacc ccgtccctac   4800
aaaaaacttt gtaaaaattt gccaggtatg gtggtgcata cctgtagtcc cagctactcg   4860
ggaggcggag gcagaaggaa tcacttgagc ccaggagttt gaggctgcag tgagctacga   4920
tcataccaca gcactccagc gtggacaaca gagtaagacc ctatctcaaa aacaaaacaa   4980
aacaaaacaa acaaaaaaaa ccacaagaaa aactgctggc tgatgcagcg gctcatgcct   5040
gtaatcccag tattttggga ggcccaggtg ggcgtatcac ctgaggtcag gagttagaga   5100
ccagcctggc caacatggtg aaaccccatc tctactaaaa atacaaaatt agccaggcat   5160
```

-continued

```
gtggcacgcg cctgtagtcc cagttactgg gaggctgaag caggaggatc acctgagccc   5220
gggaggtgga ggttgcagtg agccgagatc acaccactgc actccagcct gggtgacaca   5280
gcaataccct acctcaaaat aaaaaagaaa aagaaaagaa aagttgctgt ccccgctacc   5340
ccaatcccaa atccaaacag cctctctcat ctcacagtaa gggggaaaaa tcacccaaaa   5400
aagctaagtg atcttttgaa aacccaaact cttagaagtc taagattatt atagtcaact   5460
catgaagtgt catcataaaa gatactctaa tattatttaa gtagaaccac atattggttg   5520
tcttggtatg tctagcccct ggcatacaaa atatttaata acactgatat ggtacctgtg   5580
atgtgaaaat gtactatgag tacagcttta taaatactat atatgtacct atatacagaa   5640
aaaaatacaa caaaatcata aaagcactta tctttgaaag aggagttaca gcaattttat   5700
ttagttcttt attgctttgc tatatattct aaattttttt caatgaatat atatcacttt   5760
taaaaaaatt caatggtctt tcttataaat tatctttggc agcatgcgtt tttatatata   5820
catataaaat gtatgggaaa tttttaaagg atacattaaa ttaaagcaaa atatacaaac   5880
aaaaaatcag aatacaaaaa gataaaaaga ttgggaaggg agggagggag taaggaggaa   5940
gggtgggtgg gtatagagaa atataccaaa taatggtaag aagtggggtc ttgacacttt   6000
ctacactttt tttaaataaa aaaaattttt ttctctctct tttttttttt tagagacgaa   6060
gtctcgctat gttgcccagg ctggtcttga actcctggga tcaagagatc ctcctgcctc   6120
agcctcccaa ggtgcttgga ttacaggtgt gagccaccac gcctggtcac tttctacact   6180
ttaatatata tattttttca ttttcaatgt catttttatt agttaattta taatacccat   6240
tcaccattat attcaaagtc tatttgaaga aataaaccag aaagaatgaa atactctagc   6300
tcacatgcta ttcaatacta aattaccttt caaatcacat tcaagaagct gatgatttaa   6360
gctttggcgg tttccaataa atattggtca aaccataatt aaatctcaat atatcagtta   6420
gtacctattg agcatctcct tttacaacct aagcattgta ttaggtgctt aaatacaagc   6480
agcttgactt ttaatacatt taaaaataca tatttaagac ttaaaatctt atttatggaa   6540
ttcagttata ttttgaggtt tccagtgctg agaaatttga ggtttgtgct gtctttcagt   6600
ccccaaagct cagttctgag ttctcagact ttggtggaac ttcatgtatt gtcaggttgg   6660
cccgtaatac ctgtgggaca acttcagccc ctgtgcacat ggccaggagg ctggttgcaa   6720
acattttcag gtaggtggac caggacatgc ccctggtcat ggccaggtgg aggcatagtg   6780
ctatacagca ggcagaagtc aatattgatt tgtttttaaa gaaacatgta ctactttcat   6840
aagcagaaaa aatttctatt cttgggggaa aagattatgc cagatcctct aggattaaat   6900
gctgatgcat ctgctaaacc ttcacatatc agaacatatt tactatagaa agaatgaaaa   6960
tgggacattt gtgtgtcacc tatgtgaaca ttccaaaaat attttacaac aactaagtat   7020
tttataaatt ttatgaactg aaatttagtt caagttctag gaaaatacaa accttgctag   7080
atattataaa aatgatacaa tatatattca tttcaggctc atcagaatat atctgttatc   7140
acttgacaag aatgaaaatg caccattttg tagtgcttta aaatcaggaa gatccagagt   7200
actaaaaatg acttcttcct tgaagcttac tcaccaactt cctcccagtt actcactgct   7260
tctgccacaa gcataaacta ggacccagcc agaactccct tgaaatatac acttgcaacg   7320
attactgcat ctatcaaaat ggttcagtgc ctggctacag gttctgcaga tcgactaaga   7380
atttgaaaag tcttgtttat ttcaaaggaa gcccatgtga attctgccca gagttcatcc   7440
cagatatgca gtctaagaat acagacagat cagcagagat gtattctaaa acaggaattc   7500
tggcaatata acaaattgat ttccaatcaa aacagattta cataccatac ttatgtcaag   7560
```

-continued aagttgtttt gttttattgc atcctagatt ttattttttt gatttatggt ttactttaag 7620
cataaaaaat ttgtcaatac aactcttccc aaaaggcata aacaaaaatt cataaaactt 7680
gcatcacttg agatacttca ggtatgaatt cacaactttg ttacaactta ctatatatat 7740
gcacacatat atatatattt gggtatattg ggggggttct aatttaagaa atgcataatt 7800
ggctatagac agacagttgt cagaacttgg caatgggtac gtgcaggttc attataccaa 7860
gtctacttgt agttgttcaa aatgtatcat aatacaaggc cgggcgaggt cgtcacgcct 7920
gtaatcccag cattttggga ggctaaggca ggaggattgc ttgaggtcag gagtttgtga 7980
ccagcctggg caacagagca agaccctgtc tccaaaaaga aaaaaaataa tttttacaa 8040
aataaaaaca aaatgtatca tcagacgaaa ttaaataaga ggcaattcat ttaaatgaca 8100
acttttccca gcttgacatt taacaaaaag tctaagtcct cttaattcat atttaatgat 8160
caaatatcaa atactaattt tttttttttt tttttttttg agacggagtc tcgctctgtc 8220
gcccaggctg gagtgcagtg gcgcgatcct ggctcactgc aagctccgcc tcccgggttc 8280
acgccattct cctgcctcag cctcccgagt agctgggatt acagacatgc gccaccacgc 8340
ccggctaatt ttgtattttt agtagagatg gggtttctcc atgttggtca ggctggtctt 8400
gaatttccca cctcaggtga tctgcctgcc tcagcctcac aaagcagtag ctgggactac 8460
aggcacccac caccacactt ggttaattct tttgtatttt ttttgtaaag acgggatttc 8520
accatgttag ccaggatggt ctcgatctcc tgatctcatg atccgcccgc ctcagcctcc 8580
caaagtgctg ggattacagg cgtgagccac cccgcccggc catcaaatac taattcttaa 8640
atggtaagga cccactattc agaacctgta tccttatcac taatatgcaa atatttattg 8700
aatacttact atgtcatgca tactagagag agttagataa atttgataca gctaccctca 8760
cagaacttac agtgtaatag atggcatgac atgtacatga gtaactgtga acagtgttaa 8820
attgctattt aaaaaaaaag acggctgggc gctgtggctc atgcctgtaa tcccagcact 8880
ttgggaggcc aaggcaagtt gatcgctcga ggtcaagagt tcgagaccag cctggccaac 8940
gtggtaaaac cccgtctcta ctaaaaatac aaaaaaaaaa ttagccaggc atggtggcac 9000
aggcctgtaa tcccagctac tagggaggct gagacatgga gaactgcttg aatccaggag 9060
gcagaggtta cagtgagccg agatcatacc actacactcc agcctgagtg acagagcgag 9120
actcctgtct aaaaaaaaaa aaaaaaaaaa agatacaggt taagtgttat ggtagttgaa 9180
gagagaactc aaactctgtc tcagaagcct cacttgcatg tggaccactg atatgaaata 9240
atataaatag gtataattca ataaatagga acttcagttt taatcatccc aaacaccaaa 9300
acttcctatc aaacaggtcc aataaactca atctctataa gagctagaca gaaatctact 9360
tggtggccta taatcttatt agcccttact tgtcccatct gatattaatt aaccccatct 9420
aatatggatt agttaacaat ccagtggctg ctttgacagg aacagttgga gagagttggg 9480
gattgcaaca tattcaatta tacaaaaatg cattcagcat ctaccttgat taaggcagtg 9540
tgcaacagaa tttgcaggag agtaaaagaa tgattataaa tttacaaccc ttaaagagct 9600
atagctgggc gtggtggctc atgcctgtaa atcccagcac tttgggaggc tgaggcgggt 9660
ggatcacctg aggccagaag ttcaagacca gcctagccaa catggcgaaa ccctgtctct 9720
acaaaaaata caaaaattag ccgggtgtgg tggcacgtgc ctgtagtccc agttacttgg 9780
gaggccgagg caggagaatc gcttgaacct aggaggtgga ggctgcagtg agccgagatt 9840
gtgccactgc actccacttc agcctgggcg acaagagcaa gactccgtca caaaaaaaaa 9900

-continued

```
aaaaaaaaaa aagcttaaaa tctagtggga aaggcatata tacatacaac taactgtata   9960
gcataataaa gctcataatc tgtaacaaaa tctaattcga caagcccaga aacttgtgat  10020
ttaccaaaaa cagttatata tacacaaaaa gtaaacctag aacccaaagt tacccagcac  10080
caatgattct ctccctaagc agtatcaagt ttaaagcagt gattacattc tactgcctag  10140
attgtaaact gagtaaagga gaccagcacc tttctgctac tgaactagca cagccgtgta  10200
aaccaacaag gcaatggcag tgcccaactt tctgtatgaa tataagttac atctgtttta  10260
ttatttgtga cttggtgttg catgtggtta ttatcaacac cttctgaaag aacaactacc  10320
tgctcaggct gccataacaa aataccacag actgagtgac ttaacagaaa cttatttctc  10380
acagttttgg aggctgggaa gtccaaaatt aaggtacctg caaggtaggt ttcaatctca  10440
ggcctcttct ttggcttgaa ggtcttctaa ctgtgtgctc acatgacctc ttctaacaag  10500
ctctctggtg tctctttttt tttttttttc ttttttgaga cagagtctca ctctgtcacc  10560
caggctggag tacagtggca caatctgggc tcactgcaac ctccaactcc cgggttcaag  10620
tgattctcat gcctcaccct cccgagtagc ttggatgaca ggagcccgct accacaccca  10680
gctaattttt gtatttttag tagagatggt gtttcactac attggccagg ctggtctcaa  10740
actcctgacc tcgtgatcca cccaccttgg cctcccaaag tgctgggatt acaggtgtga  10800
gccactgcgc ccgtcctggt gtcttttcat ataagggcac taatccaatc agacctgggc  10860
ccaaccctcc cgacttcttc taactgtaat taccttccaa aggccctgtc tccaaatacc  10920
atcacactgg gggttaggac ttcaaaaaag gtatgggggg ggtgtgggag gacataaatg  10980
ctcagtccat aacaagcacc caacataaaa atggctagaa cagatcacaa aaaaaaggtc  11040
ctgtatggct tggggaaggg gctcaacccc aaaatatctg agagctctgg aggggcctag  11100
aagtggtaaa tgaatgaaaa cgtggttact ctccagatct gcctttccca aatatggcca  11160
ttcttggctg aatcagaaat caaaggacag gttattaatt actagctcta agttacttac  11220
catttgctga gacagttcag aaatctgact gcatctcctc agagatctag aacacagttc  11280
tcaaattcta acttacttgt gatatacttg tgaatgataa aaatcgctac aggtactttt  11340
attaatctga aagagtattg agaaattacc tttcattctg acttttgtct ggaatgaaaa  11400
tcaatacttt tgctataatc gattactgaa ataattttac tttccagtaa aactggcatt  11460
ataatttttt ttaattttta aaacttcata attttttgcc agactgaccc atgtaaacat  11520
acaaattact aataattatg cacgtcacat ctgtaataat ggccttcatg taaacatttt  11580
tgtggtttac acataaaatc tctaattaca aagctatatt atctaaaatt acagtaagca  11640
agaaaattaa tccaagctaa gacaatactt gcaacatcaa ttcatcatct gtgacaagga  11700
ctgcttaagt ctctttgtgg ttaaaaagga aaaaaaaaaa aaagacatgt tggccagatg  11760
cggtggctca cacctgtaat cccagcactt tgggaggctg aggtgggcgg atcacccctg  11820
gcctgcccaa catggtgaaa ccccgtctct actaaaaaca caaaaattag ctgggcgtgg  11880
tggcgggcgc ctgtaattcc agctactcgg gaggctgagg caggagaatt gctagaaccc  11940
aggaggcaga gattgcagtg agctgagatt gcaccattgc actacagtct gggcaacaaa  12000
agtgaaactc catcttaaaa aaaaaaagac aatgttcgtg ggtccaaaca agacttaatg  12060
gaagtgagtc taaaaatgag ctatgtgggc caggcgtagt ggctcccacc tgtaatccca  12120
gcactttggg aggccgaagc aggcagatca tgaggtcagg agatggagac catcctggcc  12180
aacacggtga aatcctgtct ctacaaaaat tagctgggcg tggtggtgcc tgcctgtaat  12240
cccagctact cagaaggctc aggcaggaga atcgcttgaa ccagggagtc ggtggctaga  12300
```

-continued

```
gtgagccgag atttgcatca ctgcactcct gcctggtgac agagcaagac tccatctcaa  12360
aaaaaacaaa caaaaataaa agataaaaat gagctatgtg aattaaaaga ggtataacaa  12420
tagataaacc atattttatt taattcctag taatgagtaa tatttccaaa cttctggaat  12480
gggcagaaat tgctagttgg catattttta ccttttatat tcagatacat taaaattctc  12540
aaaaaaaaac acctcaaagc agatgatccg ccatctcctt ggataatttg tgttaactca  12600
ggataacaga aaaccaaaat tatgagttac tgatgcaata ttcctaaatg taaaaataat  12660
taaagctaat agtagattca tcttccaatt tcatatcagt cttacaaata aactacatat  12720
ataacttgct tgccttccct tctgagggat aaagctgtta gaagaattaa aatcagcatt  12780
cttgactatt caaccaaggg agggataaat tattactcat tctagggaca tgggctcata  12840
actactacat gtgtaaggac atgaatttac ccaatattac aatttttcct tttattagtg  12900
tgtacagtgg aagaatagac atgttcactc tggacaaaaa aaaaattata cttatcagtt  12960
atcagaagca caatgctgaa gacagtagtt ccataacaat ttgaagtatg tgatcgaact  13020
agtagattat cttagtagta gtgaattatt gtaaatgtta gtaatttggc agccactggg  13080
cagaaaaata agaattgagg ctcaatattg atattaatgg tggtgattga cacataaatt  13140
ttatcaagtc tacacaatat aaaattacag aaaggtagaa gagtatacca gtacaacttc  13200
aacatatctt cactacaagg gagtaaaatg acatggccta gttactatct aatgaactgc  13260
agaaaactaa aagaaaactc caaggcaact cttctctgct gatctggttg gtccttttcc  13320
taccttttgc aatacccaga tacaaacaat ggatagaaaa caaagtagac ttgtagtatg  13380
caggtcacag tgctaaattc acagaaagaa acccctgaac tgaactgctc tatttcctgg  13440
tggtcacaaa gagtaattct ggtttacacc tacagattga tgtcaatcta caccctgttg  13500
ataacagtgt ggccaaggac aaaaaaaagg tgctccgttt taccaattct gtaaaaaatt  13560
attggcaggg taagctcggc tagggcagga ttacatttct aggactacca tccccgaaat  13620
ttagaagata ttatatccac ataaagcata tctttcacat taatttgcaa aaatctaaaa  13680
gctttttctt agctcaagtg tgtccaagtt taccctggca gtttaaaacg atagttacaa  13740
gcagcatggg ttgtatcaga cacatttgag ggccaatttc atgtaagtga tattgggcaa  13800
gttacttcaa ctatctgtgc ctccaaggtc atactagtgt ttatttacct aaagggtacc  13860
tgttatgtaa ctttagggtg tttacattag ataatgcctg caaaatattt acttcaacgc  13920
ctaaaacata gttaagtatt caataaatac ctactattgt cactactaac ttaaaagttt  13980
agagattaag agcagaatct ggggtgagac aaacttaggt tcaaatccta gtattgttgg  14040
gtaatcttgg gcaagttact taacctctct gatttgtgta atttaaaaaa ttagttaata  14100
tacataacag ggcttagaag agtatctagc acatagcacc atttaagcat ttgttattgc  14160
taacatgcaa acaatttaag ggaaagaaat tttttaaaaa ggaagaggga tttgcaaact  14220
aaaaacaatg agtatcttat gttcaaagaa aactaacaaa cagccagctc tagcaataat  14280
taaattcact atatactggg gcaggcatca caccccaaag ctaaaagcgt ctacctaggc  14340
caggcacggt ggctcatgcc tgtaatccca gcactttggg aagcagaggc gggcagatcg  14400
cttgagctca ggagttcaag accagcctgg acaacatggc aaaacaccat ctctacaaaa  14460
aatacaaata ttaggccggg cgcagtggct cacgcctgta atcccagcac tttgggaggc  14520
caaggcgggt ggatcacctg agatcaggag ttcgagagta gcctggccaa catggtgaaa  14580
cctcgtctct attaaaaata caaaaaatta gccaggcatg gtggcaggcg cctgtaatcc  14640
```

-continued

```
cagctactca gggggatgag gtaggagaat cgcttgaacc cgggaggcag aggttgcact  14700
gagccgagat catgccactg tactccagcc cgggcaacaa gagcgaaact ccatctcaaa  14760
aaataaataa ataaataaat aaaataaagt acaaatatta gccagggatg gtggtgcgca  14820
cctgtagtcc cagctacttg ggaggctgaa gtgggagaat cccctgagcc tggggagaat  14880
cacccgagcc cgggaagtcg aggctgcagt gagcagtgat tgtgccactg cactccatcc  14940
taggtgacag agtgagaccc tgtctcaaaa aaaagaaatt ggcagaatta agtaagttga  15000
tgtttagaga tgaaaaatca acattttttc ctcagcaact gaataaaaac aacagccact  15060
accatttttt tgagtaccta tttgtagcct attttttaac tggtattact cgagagagag  15120
agagctaggt tcgagacaga gctccttctc ttaataactg tatgacctag ggtatgtctg  15180
ttagcctctc tgaggcttca aaggttcctc atctgtaaaa tggtaataat cataccattg  15240
ctacagggct gttttgaaga ctaattagga ctatgtaagt aaacatgatg atggctatta  15300
ttactgttcc ccgccagggg ccatgcaagg gttgctgatt cacatagact gtcttataat  15360
cctctcaata actccaagag gtagccagca cctcagatat acataaaatg acttaagccc  15420
agagaggtga agtaagttgc ccacagccac acaactagta aatagcccaa acaagctgga  15480
ttcccagtta gactccgtta atagcactgc tctttacctt aagtcattac aatgcctaat  15540
atgaaataga atcgcttctt tcttagggtt caagtggtta attatttaat gtattcattc  15600
aacaaaccat catcgaggac ctcttacaag ccaagtactg tgctaagtgc tagagttacg  15660
gcggtgattc ctgcccttaa aaagttttag tgggagaaac aacaggtaac caggtcattg  15720
ccaaaacaac aaaaataatc ataataaagc aggctaaagc atatttaact ggccggggtt  15780
ttgactattt tagcaagcat gatcagaacg gttgaggagg gaggccagca gcttggccgg  15840
ttcaacaaac aagaaaaaac cagtgagggt ggagctaaga taccagaggc tgattacggt  15900
taagaatgtt cttgaaggta aggaccagat tctcattttc tatatcctgg ggcatcggtc  15960
agcatggaat ctggattcta gcacatgtga atttcggctt gaaatgacct aatgcctttt  16020
ccctagttcc ttcgtgtgtc aaatacgcat ggttaccgct accagagctg tagtggggct  16080
tcaatgaggc catgagcatc tccataaaga tgaactacag tgtgtgcaaa actaaaggca  16140
aaacctggtc cccacacgcc ctcccaggtg gtcgctttcc gtgccgaggc ccctccagag  16200
gtgccccgag aacctcacca tcgcacccca aacttccagg gaagggcctc tcccgagaaa  16260
gcccccacgc ccccaccccg cgccatcatt cccgaatctg ccctcggccc ctccccgcag  16320
cacgctcgca ggcggcacat gtcaaccaaa acgccatttc caccttctct tcccacacgc  16380
agtcctcttt tcccagggct cccccgagga gggacccacc ccaaaccccg ccattccgtc  16440
ctccctgccg ccctcgcgtg acgtaaagcc gaacccggga aactggccgc ccccgcctgc  16500
ggggttccct gggcccggcc gctctagaac tagtggatcc caattgaagg cctggtctaa  16560
atgactccaa aatcaccact taattcaaga gactgatttc cctgagtcag gcccccttaaa  16620
gcagctattt caatgggaca gggaaacaac cctaggatct ggattagaat cacttggggg  16680
ctgccacacc cccagggctc tgatcctgcc cttctcccac acgcacattc acatactgct  16740
gcagtgacct tccatttcta atgggttcct gggccatctg tcaggtatag ggaatggaaa  16800
aggggttggg gaggctctgc ttcagaaagt ttgtgtcagg ggctcccaga gcctccacag  16860
atagatagca ggggtcccca ccctaccatg gcagctataa atgtgatcaa catttattgg  16920
cctaggatac agcagttagc aaaatgcctg atgtagttcc cactccgtgg aggttgcagg  16980
ctagccaaga agtcatgagt tcagcaaccc ttacgcacca gtgggatgag attggaccag  17040
```

```
gccgagggta gtcttgggaa cactcagcat ttgtctgagg gccagaagag gctgcttgcc  17100
ctcagacagg aggtcagcat ctttattgta gcccatgaca cctctacacc attgctcttc  17160
tggtcttatg gaagacatct ttgggcctga taacagcgga gtctgtgtcc cacttgtcca  17220
ggctggagtg ccacatcagg cacactccag ttgcagggac agcacagaca agtttcagga  17280
aggctggtgg cctccaggag gttaacctta taaggccaga ttgtaaccta gttgaaaaac  17340
atacacatgc catgataata aaagaaccta ggcaccatta caagagaaaa aatcattttt  17400
gtagatacga gcatggattc ttgggtgggt cagacacact gggcttgtgc tctgactgca  17460
ctgtctcccc tacctgacct tgggtaaacc ataagactgc tgcatgactc agtgtccacc  17520
ccaaaaaagt accggtagat attggccaca gtagatatca gctagagtgg actctcatga  17580
caatgagggg agatgtattc cccatcttag gcacctggga ctctaccttc catcttctgc  17640
tccgtgtctc tccatcccca ggctcttcag aactcaggga gtccagaatg tcagctccca  17700
gatttcagcc ttcagaaagg aaacccatta ccgttcagtt gaacaaatgt tgtctgagcc  17760
ccagatctgg gctcagaggc catctaggct atgagacaag aggggaacaa agcaccgtct  17820
gcactcactc accacactca cttgctgtcc caggtcacat ccatcgggta gagaatctaa  17880
gaggctgagc tagctcccgc caccagccca gcccacccca cctggcccct tccttccttc  17940
tacaaaatat gcaccacctg tcaaagggtg ggcagtgcca ggcctgcata cagagcactg  18000
agtgtaaaag cagacatgga ccctgacctc caggagcttc caatttctt gaagagacaa  18060
atcagctggc atttcagtcc agtgtgatct gctcttggtg agcacagacc tagggagttg  18120
gggcagcttc ccagaagaac tgcagtccag gctgagggca gagaaatgag gggaatggcg  18180
aggaattggg gagcaggggg gagctcagta gagagccaag ggcgggaggt gagaagtccg  18240
tgttgggcca ggagctaccc tccggtggcc acagccgaag tcgaggatgc ctttggaact  18300
catccccact tctctctttc tgtatgtagc cgtccaagaa caagtcacct ccaagtgtag  18360
ccggatcaag gcaagccccc catctagcaa gcacttgatg ccacccagaa ctgggcttct  18420
tcagaacaat ctgagtccag gaatgatccc actcaccagg caccagagct gcgagggcat  18480
gggagtgatc tcaccaactc tggggaagcg gcaaggaatt ttcacctcca gcccccagtg  18540
tcccatcctc tcacactcag gccagactcc cctgggcaga cttgactctg tctgccagca  18600
tatgcagagc cccaaggcca ccccaccaga agtgcccctg cctgggttct gtcccagctc  18660
cctgggcacc cagtccttga gtccccacca gctcagacgg cctagtgtgc caagaatgcc  18720
cactgcgttc aacaatgctg catgggtcac agcggcagca gctgtgacca cagcagtttc  18780
ggggaaaaca cccctcagcc aagtggataa tagcgttcag cagcactcac cttctggcca  18840
ggcctgcctt cagaggccat ctgattggga ggcacaagtg cccgctgcga tgggaacaca  18900
agtgcccctg gccaacaacc ccagcttcag cctgctgggc agccagagcc tcaggcagag  18960
cccggtacag ggcccggtgc ctgtagcaaa caccaccaag ttcctccagc agggtatggc  19020
cagctttagt cccctgagcc ccatacaggg catcgagcca ccaagctatg tggctgctgc  19080
tgccaccgct gctgctgctt ctgccgttgc tgccagccag ttcccaggtc cgttcgacag  19140
aacggatatt ccccctgagc tgccacctgc cgactttttg cgccagcccc aacccccact  19200
aaatgatctg atttcgtcac ctgactgcaa tgaggtagat ttcattgaag ctctcttgaa  19260
aggctcctgt gtgagcccag atgaagactg ggtgtgcaac ttgaggctga tcgacgacat  19320
tttggaacag catgctgctg ctcaaaatgc cacagcccag aattctgggc aagtcacccc  19380
```

-continued ggatgctggg gcactttaaa tctgagcagg atgcccatag aaacccccat ggtgacatca 19440
ctctaggaag tggtgtcgat ccatacccgc agttgtctcc cgttacaatt tgagtggtgt 19500
tgtcagccca tgcttatccc tctctctacc tgtgacaaaa tggaaagctg gtgatttttc 19560
aagctacgtg tacatatttg aaaattttgt aaatggtttt cctaaacatt aatgacagaa 19620
gtatttatac ttcattttgt gactttgtaa ataaagcgac ggcttttgtt tcagtagagt 19680
tgtgtttact atgcattgtt ttgtgtttat tatacaatgt tacaaatatg cagaccgtgt 19740
tgtttgctcc agtgatacct tgttaagcta ggtggctgag tcgcttatgg ttttaatgca 19800
atgagcaatg tggatatgac caagagttgt tgtgcaagtt gacaaatgcc aaatagaaaa 19860
ccacttggcc atttatttct atgttcacta aaaatcctat tgccttgtgt gattcttaat 19920
ctcttttgcg aacctttcag tctccgctag ctctttccta atgagcttta cagcagaagc 19980
tgttttatcg ttaagtgccc cacagagaca ctttaccagg aggctgggag agttctccag 20040
atttgggaga ggcgcagaga cagtgtgtga gccgagccct gtctcagcaa tccacctgga 20100
ggagctagag tatcctcctc cctttaccat tcagaccgag agaaaaagcc cagcttgtgt 20160
gcaccctcgt ggggttaagg cgagctgttc ctggtttaaa gcctttcagt atttgttttg 20220
atgtaaggct ctgtggtttg ggggggaaca tctgtaaaca ttattagttg atttggggtt 20280
tgtctttgat ggtttctatc tgcaattatc gtcatgtata tttaagtgtc tgttatagaa 20340
aacccacacc cactgtcctg taaacttttc tcagtgtcca gactttctgt aatcacattt 20400
taattgccac ctcgtatttc acctctacat ttgaaatctg gcgtctgttt caagccagtg 20460
tgtttttttct tcgttctgta ataaacagcc aggagaaaag tgcctctatg tttttatttt 20520
tcaagggagt attcagtacc tacaaaccca agtcaggaag cctgctagtg gctttggttc 20580
tttcagaggc tgctcgatgc cttgtgtgtc agaaagaaag attcagcagt tttgcatcat 20640
ggcaaagaag cctgttattt tggggctcag cccctcattt tatagaggat gaaacagagg 20700
gggatgggag gtcacaaaga caactgcccc gggagcaggt gtgggggaga cttgccctga 20760
gggtctagac gctctgcacc accgtcctgt ctcccttgct gaagaccaca catgcccttc 20820
tttgaccaga ccctgccacc tgataggcca ggacctggta ggcgggtacc caggtttcat 20880
ggatggaacc acatctcccc aaaagtgggg aggtagctac tgggatgcac gcctcccgcc 20940
atgtgctata ggagagcagc tgaagcaaca gttgggatca gatgtagtca caattgaatg 21000
catcatcaca tttatccctc taagtggctg ggagagttga tatcctcatc cctaaggtac 21060
aaaatgttcc aatttgatca gtggctttca ggagctgaga aaggcatgtg ctctgaggca 21120
gagctgttat gtcccgcaga gcctaaaaat gctctaagaa catgctccct gccaaaattc 21180
tcaatggctg tgacaaggga caacgatcga ccaatggggg tggaagcaga cctccgcagt 21240
ccaggggcca gagctaggac agaggggtcg gagaaagagt cattttccca acactccagc 21300
tcttggccag tcctcacaca gtcccctcct gcttcctgct gagagagata tcctcatagg 21360
tctgggtaaa gtccttcagt cagctttcat tccctgtcac caactttgtc tctgttctcc 21420
ctgcccgtct caggcagcac tcctcaggaa acctctccaa gagccagcct cactgcagcg 21480
cccactattg tccctctgcc tcaagtgtcc catccatgcc aggccccagg caggctgcag 21540
ctttccctca gggccacacc aaagcacttg ggctcagctg tgctgtcccc ctccatcact 21600
gagctcaggg gcagcagggg tggggtgcca ggaggcccat tcacccttct ctggctctgt 21660
gttggaccca cctgcccagc cactgctgct tagaacctac ccgctgggaa aatgaagccc 21720
tcccggaggg gccacctcaa cctgagagcc tcacggatca cagttgtccc cactcagctc 21780

-continued

```
tgccagccct cagagaccca tagataaaag ctgagcttgg ctcgcagagc tggttccatc  21840
ttccattccc agagggttca acttcctacc ccaaccacac agggaacctc aaggctgagc  21900
cagtgtgggc tgcagtgcag accagcttcc tggacacgtc ctgccacctg accccaggct  21960
ggcctcactg cccctggcac tcctgaccct atcctcattc ctcctggcag tgcgtgttct  22020
gccattccgc tttcccttag ctgtcctctc actgtactgt cagcttctcc ttttccaggt  22080
gccccccagg ggctttccac atgaccctgt caccccacag cccatccagc accaattcca  22140
gctctctgcc acccttcaaa ggagtgacag tgccctgctt cacctcccac tcacccctca  22200
acccagagca atctggctcc agtcttgcct ccttcccccct aagtactcta gtcacagttc  22260
caaattcctc ctggtcataa agccaaatga agcttcctgg tcctcagcgg acttgccact  22320
tcagcagtac tggactctct cctcccagaa acctgtttcc ccttggctcc tggagcccac  22380
actctgctgg aatccttctg cctctctggc ctgtagcctg gccctctctc ccaacctgag  22440
gtccattctc tcctgctcct ccacaagatg ttgctccttc cattacttcc tccctctcaa  22500
ccaaagctcc ttcattagct ctttatcttc tggtttcttc ccctgggcag acgaatggat  22560
tcaagagcct gtggcccagc agcccagcac tccaggatct cagcacttca gcatcccagt  22620
accctagcat ctcaataccc cagcacccca gcaccatagt attccagcac cccattgtcc  22680
aagcatctca gcactccagc atcccagcac cccaacactc cagcagccca gaatctcagc  22740
accctagcac tgcagcatct caggacccca gcacttcagc atcccagcac actagtactc  22800
cagcatctcg gcaccccagc acctaggcat cccaacaccc agcaccccag cacttaagca  22860
tcccaccact acagtatctc aacactccag caccccagca ccatagtgtt ccagcacccc  22920
agcatcccaa caccccagca cttaagcatc ccaacacctc ggcatcccaa caccccagca  22980
ctgcagcatc tcagcacctt agcatcccag tgccctagca tctcaatgct ccagcacacc  23040
agtactacag tattccagca ccccagcact ccagcatctc agcactgcag cactgcagca  23100
ctccagcatc ccaaaatccc agcatcccaa caccccagca gaccagcaga ccagcatctc  23160
agcaccgcag catccaagga ctatcccagc atcccagcaa cccagcacct cagcatccca  23220
acaccccagc atttcagcat ggcaacaccc cagtacccca gcacttcagc accccagtat  23280
cccagcatct cagcgaccca gtatcacaaa acctcagcat cctagcaccc cagcacccca  23340
gcaccttagc accttagcat cccagcatct cagcgcctca gcatcttgat attctggctg  23400
aggtcagcgt ggtgtatcta gtcagggtcc taactttcac ttcgcaggga aatgctgctg  23460
gactgggtct catgttgggc tgaagctctc tagacccctt gaagacagca taaaagagct  23520
tggagacgct gggtgtcccc catggaagag ttcactctca tcctgctttg acaacagcct  23580
tctctggggt ccctcacggg cccctctttc ttactgcaag tttgtctctg agaagactgt  23640
gatgcagaag tcactcagct gcctgtggct cctgaagagc tgaaggtgga ggcctgtagg  23700
cctccctatg agaggcgcag aaaaaaccat gattgctagt ggggaggtgc tccctctaca  23760
acccactcca taatctgccc ccgcccagct ctgaggccag ccccagggga aaatgccaga  23820
tccccaggga ggtgtgtgag acctcagggg ctccctcctc ccttacagca ggctcaggcc  23880
cctgggggcc tcagggccaa ggtctgtggg taagctacta tctctcactt gtcctctagc  23940
cacaaaagcc agggagatct ggcaatggac atgaggttct gaagaagcac atatgactgg  24000
cttcctaatg cgtggttgtt cagtgattca ataaacacgc atgggccagg catggggaaa  24060
tagacaaaca tgatccccaa cctctcccag agtgaactgg gagggaggag tgttcatccc  24120
```

```
tcaggattac accagagaaa caaaccagca ggagatatat atggttttgg ggggtcaaga  24180
aagaggaaaa acctggcaag gcaagtccaa aatcatagga caggctgtca ggaagggcag  24240
cctggaacct ctcaagcagg agctgatgct gcagtccaca ggcagaattt cttcttcctc  24300
ggggaaatct cagctttgtt cttaaggcct ttcaactgat tggctgaggt ctgccccttc  24360
ccccacattc tccaggataa tcttccttac ttaaagtcaa ctattaatca cagctacaaa  24420
atcccttcac agctacacat agatcagtgt ttgattgacg aacagcccct acagcctagc  24480
caagttgaca cataaaacta accatcacag ggggacaaat gatgtaaaca catcaacaaa  24540
taaaacagta acaagttaag gtctatggaa aaaacacaga aggggcagag agaaagaaag  24600
caagaaggag agtcccagtt tgctagggct tgtgggaagt ggggagcagt tctctttagc  24660
taggatattt gggaaaggca tatctgaagg agtgatattt gagcttagat taaaagatgg  24720
gaaggagcaa gccatgcaaa gagctaggat gttccaagca gagacggaac agcaagtgca  24780
aatgtcagga ggaatagaag gaggctggtg ggtggggtcc agtgagcaag aggagggcag  24840
gcaggagagg ggatggggag gtgggcaggc ccagaccacc cagggccctg gagactatcc  24900
tgatccaaca agggaagcct tgagtcactt cagtgtccat gtggagaatg gacctcagac  24960
tgaatgaggg aggcagtaag gagggcctct acctccaggg cttcgccctg tggactgcgc  25020
atagacatct ccaactcaga aagtctgaac caaactttcc atagttcccc caagtctggg  25080
catcctccta ctcagtgaaa ggcagccatc acacctccct gccctgctcc cggatgcccc  25140
aaatcctctt ggtctccaag tccagaacct gagacttgtc cttgatgttt gtctttccct  25200
cacccttttct gtattctggg aagatgggtt tttttccccc agatgaatct gtaaaacttc  25260
tgtgatcaca ataaaaattc tggcagtatt attttctgga acatgacaaa gtgattcaaa  25320
attatttatc tggaagacta caaaacaaga atagccagga aatttctaaa aagaaagaag  25380
aaggaggagg agaaagaagg aggaggaaaa ggaggagaag aagaaaagaa aaagaaccaa  25440
gaaagggttc tagctctacc aaatattaaa acatatcatg aagctattta aaacaatatg  25500
gttgtggata ctgaaaaaga tgtgaataaa gtggaaggaa aataaataga aatgcacatg  25560
gggattgaga ctgtgaaaaa ggcagcatct cacatcagtg agggatgttc aacacctggt  25620
gttgggaaaa ctggctagtc atttaaacca aacaactggg tcctctacct cactcctgac  25680
attaagatac atttagatga ttcaaagagt aagacagaaa aaataacacg tgaaaacact  25740
atcagaaaac aacgtgggcc aggtgtggtg ggtcacgcct gtaatcccag cactttggga  25800
ggccgaggca gacagatcac ctgaggtggg gagttcaaga ccagcctgac caacatggtg  25860
aaatcctgtc tctactaaaa atacaaaatt agctgagcgt ggtggcgcat gcctgtaatc  25920
ccagctactc aggaggccga ggcaggagaa tcacttgaac ctgggaggca gaggttgtgg  25980
tgagccgaga tcacgccatt gcactccagc ctgggcaaca agagtgaaaa tccatctaaa  26040
aaaaaaaaaa aaagccaagg tggatatttt tatagtatca gggtagatca agcttctcca  26100
atcatgacat gaaacccaga aaccataaaa gaaaagaatg ataaaattgc ccacgtaaag  26160
taaaaagctt gcacacagaa aaacaccata caggttacaa gatgagcagc aaaatcagag  26220
aaaaaacatt gcaattcagg acacacagag gctattgttc ctaatattta aaaataaaag  26280
tagtggattg tctacaaaaa gatgaagaca agaatttcag aaaaccaaat actgcatgtt  26340
ttcacttaca agtggaagct aaacactgag tacacgtgta cacaaagaat ggaaccatag  26400
gccaggcacc gtggctcacg cctgtaatcc cagtactttg cgaggccgaa gcgggcggat  26460
cacctgaggt gaggagttcg agaccatcct ggccaacatg gtgaaaccca gtctctacta  26520
```

aaaatacaaa aattagccgg gcgtggtggt gggtgcctgt aatcccagct actcgggagg 26580
ctgcggcagt agaatcgctt gaaccctgga ggtggacctt gcagtgagcc gagatcgcac 26640
cactgcactc cagcctgggc aacagagtga gactccatct caaaaaaaaa aaaaaggaat 26700
agaacaatag acactggggc ctacttgagg gaggagggtg aggatcaaaa acctgcctat 26760
caggtactat gcttattacc tgggtggtga aataatctgt acaccaaacc ccagtgacat 26820
gcaatttacc gatgtaacaa acctgcccat gtacccgctg aacctaaaat aaaagttgga 26880
aaaaaatata gaaatttttct ttgtaatagc caaaaactgc aaacagccca ggtgtctatt 26940
agtagaatgc ataaacaaac tcgggcatgt tcatacaatg taaaactact catcaataaa 27000
aagtgatact tctcagcaat gaaaagaaac tagctactga taccagctac aacatggatg 27060
gatttcaagt gctttatgat gagagcaaga agccagacac aaaagtgtct atatatatat 27120
acagtatata tacgtatata tacacatata tacagtatat atatacatat acatgtatat 27180
atatactgta tatatactgt atatatatac acagtatata tatacatata tacagtgtat 27240
atatactgtg tatatataca tgtatatata ctgtgtatat atacatgtat atatactgtg 27300
tatatataca tgtatatata ctgtgtatat atacatgtat atatatgtat actgtatata 27360
tactgtatat atatatacac atatatacag tatatatata cagtatatac tgtatatata 27420
cagtatatac gtgtatatat acatatatac agtatatatg taaatataca tatatacagt 27480
atatatgtaa atatacatat atacatgtat atatatacac tatatatata catatatagt 27540
gtatatatac atatatacat gtatatattt actatatgat tccatttata taaagtgcca 27600
aaacagtcaa aaataatcta tgtggaaaaa atcaacaaag ggatcccccg ggctgcagga 27660
attcgatggc gcgccgacgt cgcatgctcc tctagactcg aggaattcgg taccccgggt 27720
tcgaaatcga taagcttgga tcggccgcaa taaaatatct ttattttcat tacatctgtg 27780
tgttggtttt ttgtgtgaat cgtaactaac atacgctctc catcaaaaca aaacgaaaca 27840
aaacaaacta gcaaaatagg ctgtccccag tgcaagtgca ggtgccagaa catttctcta 27900
tcgaggatct gcgatcgctg aattctgggg actttccact ggggactttc cactggggac 27960
tttccactgg ggactttcca ctggggactt tccactcctg cagcagtgga tattcccaga 28020
aaactttttg gatgcagttg ggatttcct ctttactgga tgtggacaat atcctcctat 28080
tattcacagg aagcaatccc tcctataaaa gggcctcaga ggaagtagtg ttcagctgtt 28140
cttggctgac ttcacatcaa agctcctata ctgacctgag acagagccat gaattccgtt 28200
ttttttttt tttttggaaa tatgagggtt tttccgcttc tgacagtgga acggaatgac 28260
agcagcacag gctggtgaat gactactttc tttataagca accaccttga gcctgaaatg 28320
gcagtcgcta gtctctattg ccttgctgtg gcctcgggat ggaaatctgc tggggaccct 28380
acagtcacct aatctctctc cttctcatcc ttctgtttca ttcagaggca gcctgccgcc 28440
cttctgggaa aagaccctgc aagatgcaag ccttcagaat ctgggatact aaccagaaga 28500
ccttttacct gagaaacaac cagctcattg ctgggtactt acaaggacca aatatcaaac 28560
tagaagaaaa gatagacatg gtgcctattg accttcatag tgtgttcttg ggcatccacg 28620
ggggcaagct gtgcctgtct tgtgccaagt ctggagatga tatcaagctc cagctggagg 28680
aagttaacat cactgatctg agcaagaaca aagaagaaga caagcgcttt accttcatcc 28740
gctctgagaa aggccccacc accagctttg agtcagctgc ctgtccagga tggttcctct 28800
gcacaacact agaggctgac cgtcctgtga gcctcaccaa cacaccggaa gagcccctta 28860

-continued tagtcacgaa gttctacttc caggaagacc aatagtctag ctcgacatga taagatacat 28920
tgatgagttt ggacaaacca caactagaat gcagtgaaaa aaatgcttta tttgtgaaat 28980
ttgtgatgct attgctttat ttgtgaaatt tgtgatgcta ttgctttatt tgtaaccatt 29040
ataagctgca ataaacaagt taacaacaac aattgcattc attttatgtt tcaggttcag 29100
ggggaggtgt gggaggtttt ttaaagcaag taaaacctct acaaatgtgg tagatccatt 29160
taaatgttag atccggagag ctcccaacgc gttgggtcga cggcgcgcct accagtaaaa 29220
aagaaaacct attaaaaaaa caccactcga cacggcacca gctcaatcag tcacagtgta 29280
aaaaagggcc aagtgcagag cgagtatata taggactaaa aaatgacgta acggttaaag 29340
tccacaaaaa acacccagaa aaccgcacgc gaacctacgc ccagaaacga aagccaaaaa 29400
acccacaact tcctcaaatc gtcacttccg ttttcccacg ttacgtcact tcccatttta 29460
agaaaactac aattcccaac acatacaagt tactccgccc taaaacctac gtcacccgcc 29520
ccgttcccac gccccgcgcc acgtcacaaa ctccaccccc tcattatcat attggcttca 29580
atccaaaata aggtatatta ttgatgatgt tt 29612

<210> SEQ ID NO 3
<211> LENGTH: 29273
<212> TYPE: DNA
<213> ORGANISM: Artificial sequence
<220> FEATURE:
<223> OTHER INFORMATION: /note="Description of Artificial sequence:
Equine helper-dependent adenovirus-Il1-Ra"
<220> FEATURE:
<221> NAME/KEY: source
<222> LOCATION: (1)..(29273)
<223> OTHER INFORMATION: /note="Description of Artificial sequence:
Equine helper-dependent adenovirus-Il1-Ra"
<220> FEATURE:
<221> NAME/KEY: source
<222> LOCATION: (1)..(29273)

<400> SEQUENCE: 3
aaacatcatc aataatatac cttattttgg attgaagcca atatgataat gaggggtgg 60 agtttgtgac gtggcgcggg gcgtgggaac ggggcgggtg acgtagtagt gtggcggaag 120
tgtgatgttg caagtgtggc ggaacacatg taagcgacgg atgtggcaaa agtgacgttt 180
ttggtgtgcg ccggtgtaca caggaagtga caattttcgc gcggttttag gcggatgttg 240
tagtaaattt gggcgtaacc gagtaagatt tggccatttt cgcgggaaaa ctgaataaga 300
ggaagtgaaa tctgaataat tttgtgttac tcatagcgcg taatatttgt ctagggccgc 360
ggggactttg accgtttacg tggagactcg cccaggtgtt tttctcaggt gttttccgcg 420
ttccgggtca aagttggcgt tttgatatca agcttatcga taccgtaaac aagtctttaa 480
ttcaagcaag actttaacaa gttaaaagga gcttatgggt aggaagtagt gttatgatgt 540
atgggcataa agggttttaa tgggatagtg aaaatgtcta taataatact taaatggctg 600
cccaatcacc tacaggattg atgtaaacat ggaaaaggtc aaaaacttgg gtcactaaaa 660
tagatgatta atggagagga tgaggttgat agttaaatgt agataagtgg tcttattctc 720
aataaaaatg tgaacataag gcgagtttct acaaagatgg acaggactca ttcatgaaac 780
agcaaaaact ggacatttgt tctaatcttt gaagagtatg aaaaattcct attttaaagg 840
taaaacagta actcacagga aataccaacc caacataaaa tcagaaacaa tagtctaaag 900
taataaaaat caaacgtttg cacgatcaaa ttatgaatga aattcactac taaaattcac 960
actgattttg tttcatccac agtgtcaatg ttgtgatgca tttcaattgt gtgacacagg 1020

```
cagactgtgg atcaaaagtg gtttctggtg cgacttactc tcttgagtat acctgcagtc   1080
ccctttctta agtgtgttaa aaaaaaaggg ggatttcttc aattcgccaa tactctagct   1140
ctccatgtgc tttctaggaa acaagtgtta acccacctta tttgtcaaac ctagctccaa   1200
aggacttttg actccccaca aaccgatgta gctcaagaga gggtatctgt caccagtatg   1260
tatagtgaaa aaagtatccc aagtcccaac agcaattcct aaaaggagtt tatttaaaaa   1320
accacacaca cctgtaaaat aagtatatat cctccaaggt gactagtttt aaaaaaacag   1380
tattggcttt gatgtaaagt actagtgaat atgttagaaa aatctcactg taaccaagtg   1440
aaatgaaagc aagtatggtt tgcagagatt caaagaaaat ataagaaaac ctactgttgc   1500
cactaaaaag aatcatatat taaatatact cacacaatag ctcttcagtc tgataaaatc   1560
tacagtcata ggaatggatc tatcactatt tctattcagt gctttgatgt aatccagcag   1620
gtcagcaaag aatttatagc ccccccttgag cacacagagg gctacaatgt gatggcctcc   1680
catctccttc atcacatctc gagcaagacg ttcagtccta cagaaataaa atcaggaatt   1740
taatagaaag tttcatacat taaactttat aacaaacacc tcttagtcat taaacttcca   1800
caccaacctg ggcaatatag tgagacccca tgcctgcaaa aaaaaaaaaa ttagccaggc   1860
atggtagcat gtacctgtag tcccagctac ttgagaggtg aggtgggaaa atcactttag   1920
tgcaggatgt tgaggctgga gtgaactgtg attgtgccac tgcactccag cctggacaat   1980
agagcaagac cttgtctcaa aaaaatgcat taaaaatttt ttttaaatct tccacgtatc   2040
acatcctttg ccctcatgtt tcataaggta aaaaatttga taccttcaaa aaaaccaagc   2100
ataccactat cataattttt tttaaatgca aataaaaaca agataccatt ttcacctatc   2160
agactggcag gttctgatta aatgaaattt tctggataat atacaatatt aagagagact   2220
gtagaaactg ggccagtggc tcatgcctgt aatcccagca ctttgggagg ctgggtaaca   2280
tggcgaaccc tgtttctaca aaataaaaat attagctggg agtggtggcg cacacctata   2340
gtcccagcta ctcaggaggc tgaggtggaa ggatcgcttg aacccaggag gttgagactg   2400
cagtgaactg tgatcattct gctgcactgc accccagcct gggcaacaga gaccttgtct   2460
caaaaaaaaa aaaaaaagag acaaattgtg aagagaaagg tactctcata taacatcagg   2520
agtataaaat gattcaactt cttagaggaa aatttggcaa taccaaaata ttcaataaac   2580
tctttcccct tgacccagaa attccacttg aataaagctg aacaagtacc aaacatgtaa   2640
aagaatgttt cttctagtac agtcggtaag aacaaaatag tgtctatcaa tagtggactg   2700
gttaaatcag ttatggtatc tccataagac agaatgctat gcaaccttta aaatatatta   2760
gatagctcta gacacactaa tattaaaagt gtccaataac atttaaaact atactcatac   2820
gttaaaatat aaatgtatat atgtactttt gcatatagta tacatgcata ggccagtgct   2880
tgagaagaaa tgtgtacaga aggctgaaag gagagaactt tagtcttctt gtttatggcc   2940
tccatagtta gaatatttta taacacaaat attttgatat tataatttta aaataaaaac   3000
acagaatagc cagacataca atgcaagcat tcaataccag gtaaggtttt tcactgtaat   3060
tgacttaaca gaaaattttc aagctagatg tgcataataa taaaaatctg accttgcctt   3120
catgtgattc agccccagtc cattaccctg tttaggactg agaaatgcaa gactctggct   3180
agagttcctt cttccatctc ccttcaatgt ttactttgtt ctggtcccta cagagtccca   3240
ctataccaca actgatacta agtaattagt aaggccctcc tcttttattt ttaataaaga   3300
agattttaga aagcatcagt tatttaataa gttggcctag tttatgttca aatagcaagt   3360
actcagaaca gctgctgatg tttgaaatta acacaagaaa aagtaaaaaa cctcatttta   3420
```

```
agatcttact tacctgtcca taattagtcc atgaggaata aacacccttt ccaaatcctc   3480
agcataatga ttaggtatgc aaaataaatc aaggtcataa cctggttcat catcactaat   3540
ctgaaaaaga aatatagctg tttcaatgag agcattacag gatacaaaca tttgattgga   3600
ttaagatgtt aaaaaataac cttagtctat cagagaaatt taggtgtaag atgatattag   3660
taactgttaa ctttgtaggt atgataatga attatgtaag aaaacaacag gccgggcggg   3720
ttggttcaca cgtgtaatcc cagcactttg ggaggctgag gcaggcagac tgcctgagct   3780
caggagttcg agaccagcct gggcaacacg gtgaaatccc gtctctacta aaaatacaaa   3840
aaaattagcc gggtgtggtg acacatgcct gtagtcccag ctacttggga ggctgaggca   3900
ggagaatcac ttgaacctgg gaggtgaagg ttgcagtgag ccaagatggc accacttcac   3960
tccagcctgg gaaacagagc aagactctgt ctctgagctg agatggcacc acttcactcc   4020
agcctgggaa acagagcaag actctgtctc aaaaaaaaca aaacacacaa acaaaaaaac   4080
aggctgggcg cggtggctca cgcctgtaat cccagcactt tgggaggccg aggcgggtgg   4140
atcacctgag gtcaggagtt ccagaccagc cttgtcaaca tggtgaaacc tccccccgcc   4200
gtctctacta aaaatacaaa aattagccag gcgtggtggc aggagcctgt aatcccagct   4260
acttgggagg ctgaggcagg agaatcgctt gtacccagaa ggcagaggtt gcactgagct   4320
gagatggcac cattgcactc cagcctgggg gacaagagcg agatttcgtc tttaaaaaac   4380
aaaaacaaaa caaaaaacca tgtaactata tgtcttagtc atcttagtca agaatgtaga   4440
agtaaagtga taagatatgg aatttccttt aggtcacaaa gagaaaaaga aaaattttaa   4500
agagctaaga caaacgcagc aaaatcttta tatttaataa tattctaaac atgggtgatg   4560
aacatacggg tattcattat actattctct ccacttttga gtatgtttga aaatttagta   4620
aaacaagttt taacacactg tagtctaaca agataaaata tcacactgaa caggaaaaac   4680
tggcatggtg tggtggctca cacttgtaat cccagtgctt tgggaggctg agacaggaga   4740
gttgcttgag gccaggagtt caagaccgac atggggaatg tagcaagacc ccgtccctac   4800
aaaaaacttt gtaaaaattt gccaggtatg gtggtgcata cctgtagtcc cagctactcg   4860
ggaggcggag gcagaaggaa tcacttgagc ccaggagttt gaggctgcag tgagctacga   4920
tcataccaca gcactccagc gtggacaaca gagtaagacc ctatctcaaa aacaaaacaa   4980
aacaaaacaa acaaaaaaaa ccacaagaaa aactgctggc tgatgcagcg gctcatgcct   5040
gtaatcccag tattttggga ggcccaggtg ggcgtatcac ctgaggtcag gagttagaga   5100
ccagcctggc caacatggtg aaaccccatc tctactaaaa atacaaaatt agccaggcat   5160
gtggcacgcg cctgtagtcc cagttactgg gaggctgaag caggaggatc acctgagccc   5220
gggaggtgga ggttgcagtg agccgagatc acaccactgc actccagcct gggtgacaca   5280
gcaataccct acctcaaaat aaaaaagaaa aagaaaagaa aagttgctgt ccccgctacc   5340
ccaatcccaa atccaaacag cctctctcat ctcacagtaa gggggaaaaa tcacccaaaa   5400
aagctaagtg atcttttgaa aacccaaact cttagaagtc taagattatt atagtcaact   5460
catgaagtgt catcataaaa gatactctaa tattatttaa gtagaaccac atattggttg   5520
tcttggtatg tctagcccct ggcatacaaa atatttaata acactgatat ggtacctgtg   5580
atgtgaaaat gtactatgag tacagcttta taaatactat atatgtacct atatacagaa   5640
aaaaatacaa caaaatcata aaagcactta tctttgaaag aggagttaca gcaattttat   5700
ttagttcttt attgctttgc tatatattct aaattttttt caatgaatat atatcacttt   5760
```

-continued

```
taaaaaaatt caatggtctt tcttataaat tatctttggc agcatgcgtt tttatatata   5820
catataaaat gtatgggaaa tttttaaagg atacattaaa ttaaagcaaa atatacaaac   5880
aaaaaatcag aatacaaaaa gataaaaaga ttgggaaggg agggagggag taaggaggaa   5940
gggtgggtgg gtatagagaa atataccaaa taatggtaag aagtggggtc ttgacacttt   6000
ctacactttt tttaaataaa aaaaattttt ttctctctct tttttttttt tagagacgaa   6060
gtctcgctat gttgcccagg ctggtcttga actcctggga tcaagagatc ctcctgcctc   6120
agcctcccaa ggtgcttgga ttacaggtgt gagccaccac gcctggtcac tttctacact   6180
ttaatatata tattttttca ttttcaatgt catttttatt agttaattta taatacccat   6240
tcaccattat attcaaagtc tatttgaaga aataaaccag aaagaatgaa atactctagc   6300
tcacatgcta ttcaatacta aattaccttt caaatcacat tcaagaagct gatgatttaa   6360
gctttggcgg tttccaataa atattggtca aaccataatt aaatctcaat atatcagtta   6420
gtacctattg agcatctcct tttacaacct aagcattgta ttaggtgctt aaatacaagc   6480
agcttgactt ttaatacatt taaaaataca tatttaagac ttaaaatctt atttatggaa   6540
ttcagttata ttttgaggtt tccagtgctg agaaatttga ggtttgtgct gtctttcagt   6600
ccccaaagct cagttctgag ttctcagact ttggtggaac ttcatgtatt gtcaggttgg   6660
cccgtaatac ctgtgggaca acttcagccc ctgtgcacat ggccaggagg ctggttgcaa   6720
acattttcag gtaggtggac caggacatgc ccctggtcat ggccaggtgg aggcatagtg   6780
ctatacagca ggcagaagtc aatattgatt tgtttttaaa gaaacatgta ctactttcat   6840
aagcagaaaa aatttctatt cttgggggaa aagattatgc cagatcctct aggattaaat   6900
gctgatgcat ctgctaaacc ttcacatatc agaacatatt tactatagaa agaatgaaaa   6960
tgggacattt gtgtgtcacc tatgtgaaca ttccaaaaat attttacaac aactaagtat   7020
tttataaatt ttatgaactg aaatttagtt caagttctag gaaaatacaa accttgctag   7080
atattataaa aatgatacaa tatatattca tttcaggctc atcagaatat atctgttatc   7140
acttgacaag aatgaaaatg caccattttg tagtgcttta aaatcaggaa gatccagagt   7200
actaaaaatg acttcttcct tgaagcttac tcaccaactt cctcccagtt actcactgct   7260
tctgccacaa gcataaacta ggacccagcc agaactccct tgaaatatac acttgcaacg   7320
attactgcat ctatcaaaat ggttcagtgc ctggctacag gttctgcaga tcgactaaga   7380
atttgaaaag tcttgtttat ttcaaaggaa gcccatgtga attctgccca gagttcatcc   7440
cagatatgca gtctaagaat acagacagat cagcagagat gtattctaaa acaggaattc   7500
tggcaatata acaaattgat ttccaatcaa aacagattta cataccatac ttatgtcaag   7560
aagttgtttt gttttattgc atcctagatt ttattttttt gatttatggt ttactttaag   7620
cataaaaaat ttgtcaatac aactcttccc aaaaggcata aacaaaaatt cataaaactt   7680
gcatcacttg agatacttca ggtatgaatt cacaactttg ttacaactta ctatatatat   7740
gcacacatat atatatattt gggtatattg ggggggttct aatttaagaa atgcataatt   7800
ggctatagac agacagttgt cagaacttgg caatgggtac gtgcaggttc attataccaa   7860
gtctacttgt agttgttcaa aatgtatcat aatacaaggc cgggcgaggt cgtcacgcct   7920
gtaatcccag cattttggga ggctaaggca ggaggattgc ttgaggtcag gagtttgtga   7980
ccagcctggg caacagagca agaccctgtc tccaaaaaga aaaaaaataa tttttttacaa   8040
aataaaaaca aaatgtatca tcagacgaaa ttaaataaga ggcaattcat ttaaatgaca   8100
acttttccca gcttgacatt taacaaaaag tctaagtcct cttaattcat atttaatgat   8160
```

```
caaatatcaa atactaattt tttttttttt tttttttttg agacggagtc tcgctctgtc   8220
gcccaggctg gagtgcagtg gcgcgatcct ggctcactgc aagctccgcc tcccgggttc   8280
acgccattct cctgcctcag cctcccgagt agctgggatt acagacatgc gccaccacgc   8340
ccggctaatt ttgtattttt agtagagatg gggtttctcc atgttggtca ggctggtctt   8400
gaatttccca cctcaggtga tctgcctgcc tcagcctcac aaagcagtag ctgggactac   8460
aggcacccac caccacactt ggttaattct tttgtatttt ttttgtaaag acgggatttc   8520
accatgttag ccaggatggt ctcgatctcc tgatctcatg atccgcccgc ctcagcctcc   8580
caaagtgctg ggattacagg cgtgagccac cccgcccggc catcaaatac taattcttaa   8640
atggtaagga cccactattc agaacctgta tccttatcac taatatgcaa atatttattg   8700
aatacttact atgtcatgca tactagagag agttagataa atttgataca gctaccctca   8760
cagaacttac agtgtaatag atggcatgac atgtacatga gtaactgtga acagtgttaa   8820
attgctattt aaaaaaaaag acggctgggc gctgtggctc atgcctgtaa tcccagcact   8880
ttgggaggcc aaggcaagtt gatcgctcga ggtcaagagt tcgagaccag cctggccaac   8940
gtggtaaaac cccgtctcta ctaaaaatac aaaaaaaaaa ttagccaggc atggtggcac   9000
aggcctgtaa tcccagctac tagggaggct gagacatgga gaactgcttg aatccaggag   9060
gcagaggtta cagtgagccg agatcatacc actacactcc agcctgagtg acagagcgag   9120
actcctgtct aaaaaaaaaa aaaaaaaaaa agatacaggt taagtgttat ggtagttgaa   9180
gagagaactc aaactctgtc tcagaagcct cacttgcatg tggaccactg atatgaaata   9240
atataaatag gtataattca ataaatagga acttcagttt taatcatccc aaacaccaaa   9300
acttcctatc aaacaggtcc aataaactca atctctataa gagctagaca gaaatctact   9360
tggtggccta taatcttatt agcccttact tgtcccatct gatattaatt aaccccatct   9420
aatatggatt agttaacaat ccagtggctg ctttgacagg aacagttgga gagagttggg   9480
gattgcaaca tattcaatta tacaaaaatg cattcagcat ctaccttgat taaggcagtg   9540
tgcaacagaa tttgcaggag agtaaaagaa tgattataaa tttacaaccc ttaaagagct   9600
atagctgggc gtggtggctc atgcctgtaa atcccagcac tttgggaggc tgaggcgggt   9660
ggatcacctg aggccagaag ttcaagacca gcctagccaa catggcgaaa ccctgtctct   9720
acaaaaaata caaaaattag ccgggtgtgg tggcacgtgc ctgtagtccc agttacttgg   9780
gaggccgagg caggagaatc gcttgaacct aggaggtgga ggctgcagtg agccgagatt   9840
gtgccactgc actccacttc agcctgggcg acaagagcaa gactccgtca caaaaaaaaa   9900
aaaaaaaaaa aagcttaaaa tctagtggga aaggcatata tacatacaac taactgtata   9960
gcataataaa gctcataatc tgtaacaaaa tctaattcga caagcccaga aacttgtgat  10020
ttaccaaaaa cagttatata tacacaaaaa gtaaacctag aacccaaagt tacccagcac  10080
caatgattct ctccctaagc agtatcaagt ttaaagcagt gattacattc tactgcctag  10140
attgtaaact gagtaaagga gaccagcacc tttctgctac tgaactagca cagccgtgta  10200
aaccaacaag gcaatggcag tgcccaactt tctgtatgaa tataagttac atctgtttta  10260
ttatttgtga cttggtgttg catgtggtta ttatcaacac cttctgaaag aacaactacc  10320
tgctcaggct gccataacaa aataccacag actgagtgac ttaacagaaa cttatttctc  10380
acagttttgg aggctgggaa gtccaaaatt aaggtacctg caaggtaggt ttcaatctca  10440
ggcctcttct ttggcttgaa ggtcttctaa ctgtgtgctc acatgacctc ttctaacaag  10500
```

```
ctctctggtg tctctttttt tttttttttc ttttttgaga cagagtctca ctctgtcacc  10560
caggctggag tacagtggca caatctgggc tcactgcaac ctccaactcc cgggttcaag  10620
tgattctcat gcctcaccct cccgagtagc ttggatgaca ggagcccgct accacaccca  10680
gctaattttt gtatttttag tagagatggt gtttcactac attggccagg ctggtctcaa  10740
actcctgacc tcgtgatcca cccaccttgg cctcccaaag tgctgggatt acaggtgtga  10800
gccactgcgc ccgtcctggt gtcttttcat ataagggcac taatccaatc agacctgggc  10860
ccaaccctcc cgacttcttc taactgtaat taccttccaa aggccctgtc tccaaatacc  10920
atcacactgg gggttaggac ttcaaaaaag gtatgggggg ggtgtgggag gacataaatg  10980
ctcagtccat aacaagcacc caacataaaa atggctagaa cagatcacaa aaaaaaggtc  11040
ctgtatggct ttggggaagg gctcaacccc aaaatatctg agagctctgg aggggcctag  11100
aagtggtaaa tgaatgaaaa cgtggttact ctccagatct gcctttccca aatatggcca  11160
ttcttggctg aatcagaaat caaaggacag gttattaatt actagctcta agttacttac  11220
catttgctga gacagttcag aaatctgact gcatctcctc agagatctag aacacagttc  11280
tcaaattcta acttacttgt gatatacttg tgaatgataa aaatcgctac aggtactttt  11340
attaatctga aagagtattg agaaattacc tttcattctg acttttgtct ggaatgaaaa  11400
tcaatacttt tgctataatc gattactgaa ataattttac tttccagtaa aactggcatt  11460
ataatttttt ttaattttta aaacttcata attttttgcc agactgaccc atgtaaacat  11520
acaaattact aataattatg cacgtcacat ctgtaataat ggccttcatg taaacatttt  11580
tgtggtttac acataaaatc tctaattaca aagctatatt atctaaaatt acagtaagca  11640
agaaaattaa tccaagctaa gacaatactt gcaacatcaa ttcatcatct gtgacaagga  11700
ctgcttaagt ctctttgtgg ttaaaaagga aaaaaaaaaa aaagacatgt tggccagatg  11760
cggtggctca cacctgtaat cccagcactt tgggaggctg aggtgggcgg atcacccctg  11820
gcctgcccaa catggtgaaa ccccgtctct actaaaaaca caaaaaattag ctgggcgtgg  11880
tggcgggcgc ctgtaattcc agctactcgg gaggctgagg caggagaatt gctagaaccc  11940
aggaggcaga gattgcagtg agctgagatt gcaccattgc actacagtct gggcaacaaa  12000
agtgaaactc catcttaaaa aaaaaaagac aatgttcgtg ggtccaaaca agacttaatg  12060
gaagtgagtc taaaaatgag ctatgtgggc caggcgtagt ggctcccacc tgtaatccca  12120
gcactttggg aggccgaagc aggcagatca tgaggtcagg agatggagac catcctggcc  12180
aacacggtga aatcctgtct ctacaaaaat tagctgggcg tggtggtgcc tgcctgtaat  12240
cccagctact cagaaggctc aggcaggaga atcgcttgaa ccagggagtc ggtggctaga  12300
gtgagccgag atttgcatca ctgcactcct gcctggtgac agagcaagac tccatctcaa  12360
aaaaaacaaa caaaaataaa agataaaaat gagctatgtg aattaaaaga ggtataacaa  12420
tagataaacc atattttatt taattcctag taatgagtaa tatttccaaa cttctggaat  12480
gggcagaaat tgctagttgg catattttta ccttttatat tcagatacat taaaattctc  12540
aaaaaaaaac acctcaaagc agatgatccg ccatctcctt ggataatttg tgttaactca  12600
ggataacaga aaaccaaaat tatgagttac tgatgcaata ttcctaaatg taaaaataat  12660
taaagctaat agtagattca tcttccaatt tcatatcagt cttacaaata aactacatat  12720
ataacttgct tgccttccct tctgagggat aaagctgtta gaagaattaa aatcagcatt  12780
cttgactatt caaccaaggg agggataaat tattactcat tctagggaca tgggctcata  12840
actactacat gtgtaaggac atgaatttac ccaatattac aatttttcct tttattagtg  12900
```

```
tgtacagtgg aagaatagac atgttcactc tggacaaaaa aaaaattata cttatcagtt  12960
atcagaagca caatgctgaa gacagtagtt ccataacaat ttgaagtatg tgatcgaact  13020
agtagattat cttagtagta gtgaattatt gtaaatgtta gtaatttggc agccactggg  13080
cagaaaaata agaattgagg ctcaatattg atattaatgg tggtgattga cacataaatt  13140
ttatcaagtc tacacaatat aaaattacag aaaggtagaa gagtatacca gtacaacttc  13200
aacatatctt cactacaagg gagtaaaatg acatggccta gttactatct aatgaactgc  13260
agaaaactaa aagaaaactc caaggcaact cttctctgct gatctggttg gtccttttcc  13320
taccttttgc aatacccaga tacaaacaat ggatagaaaa caaagtagac ttgtagtatg  13380
caggtcacag tgctaaattc acagaaagaa acccctgaac tgaactgctc tatttcctgg  13440
tggtcacaaa gagtaattct ggtttacacc tacagattga tgtcaatcta caccctgttg  13500
ataacagtgt ggccaaggac aaaaaaaagg tgctccgttt taccaattct gtaaaaaatt  13560
attggcaggg taagctcggc tagggcagga ttacatttct aggactacca tccccgaaat  13620
ttagaagata ttatatccac ataaagcata tctttcacat taatttgcaa aaatctaaaa  13680
gctttttctt agctcaagtg tgtccaagtt taccctggca gtttaaaacg atagttacaa  13740
gcagcatggg ttgtatcaga cacatttgag ggccaatttc atgtaagtga tattgggcaa  13800
gttacttcaa ctatctgtgc ctccaaggtc atactagtgt ttatttacct aaagggtacc  13860
tgttatgtaa ctttagggtg tttacattag ataatgcctg caaaatattt acttcaacgc  13920
ctaaaacata gttaagtatt caataaatac ctactattgt cactactaac ttaaaagttt  13980
agagattaag agcagaatct ggggtgagac aaacttaggt tcaaatccta gtattgttgg  14040
gtaatcttgg gcaagttact taacctctct gatttgtgta atttaaaaaa ttagttaata  14100
tacataacag ggcttagaag agtatctagc acatagcacc atttaagcat ttgttattgc  14160
taacatgcaa acaatttaag ggaaagaaat tttttaaaaa ggaagaggga tttgcaaact  14220
aaaaacaatg agtatcttat gttcaaagaa aactaacaaa cagccagctc tagcaataat  14280
taaattcact atatactggg gcaggcatca caccccaaag ctaaaagcgt ctacctaggc  14340
caggcacggt ggctcatgcc tgtaatccca gcactttggg aagcagaggc gggcagatcg  14400
cttgagctca ggagttcaag accagcctgg acaacatggc aaaacaccat ctctacaaaa  14460
aatacaaata ttaggccggg cgcagtggct cacgcctgta atcccagcac tttgggaggc  14520
caaggcgggt ggatcacctg agatcaggag ttcgagagta gcctggccaa catggtgaaa  14580
cctcgtctct attaaaaata caaaaaatta gccaggcatg gtggcaggcg cctgtaatcc  14640
cagctactca gggggatgag gtaggagaat cgcttgaacc cgggaggcag aggttgcact  14700
gagccgagat catgccactg tactccagcc cgggcaacaa gagcgaaact ccatctcaaa  14760
aaataaataa ataaataaat aaaataaagt acaaatatta gccagggatg gtggtgcgca  14820
cctgtagtcc cagctacttg ggaggctgaa gtgggagaat cccctgagcc tggggagaat  14880
cacccgagcc cgggaagtcg aggctgcagt gagcagtgat tgtgccactg cactccatcc  14940
taggtgacag agtgagaccc tgtctcaaaa aaaagaaatt ggcagaatta agtaagttga  15000
tgtttagaga tgaaaaatca acattttttc ctcagcaact gaataaaaac aacagccact  15060
accatttttt tgagtaccta tttgtagcct attttttaac tggtattact cgagagagag  15120
agagctaggt tcgagacaga gctccttctc ttaataactg tatgacctag ggtatgtctg  15180
ttagcctctc tgaggcttca aaggttcctc atctgtaaaa tggtaataat cataccattg  15240
```

-continued

```
ctacagggct gttttgaaga ctaattagga ctatgtaagt aaacatgatg atggctatta  15300
ttactgttcc ccgccagggg ccatgcaagg gttgctgatt cacatagact gtcttataat  15360
cctctcaata actccaagag gtagccagca cctcagatat acataaaatg acttaagccc  15420
agagaggtga agtaagttgc ccacagccac acaactagta aatagcccaa acaagctgga  15480
ttcccagtta gactccgtta atagcactgc tctttacctt aagtcattac aatgcctaat  15540
atgaaataga atcgcttctt tcttagggtt caagtggtta attatttaat gtattcattc  15600
aacaaaccat catcgaggac ctcttacaag ccaagtactg tgctaagtgc tagagttacg  15660
gcggtgattc ctgcccttaa aaagttttag tgggagaaac aacaggtaac caggtcattg  15720
ccaaaacaac aaaaataatc ataataaagc aggctaaagc atatttaact ggccggggtt  15780
ttgactattt tagcaagcat gatcagaacg gttgaggagg gaggccagca gcttggccgg  15840
ttcaacaaac aagaaaaaac cagtgagggt ggagctaaga taccagaggc tgattacggt  15900
taagaatgtt cttgaaggta aggaccagat tctcattttc tatatcctgg ggcatcggtc  15960
agcatggaat ctggattcta gcacatgtga atttcggctt gaaatgacct aatgcctttt  16020
ccctagttcc ttcgtgtgtc aaatacgcat ggttaccgct accagagctg tagtggggct  16080
tcaatgaggc catgagcatc tccataaaga tgaactacag tgtgtgcaaa actaaaggca  16140
aaacctggtc cccacacgcc ctcccaggtg gtcgctttcc gtgccgaggc ccctccagag  16200
gtgccccgag aacctcacca tcgcacccca aacttccagg gaagggcctc tcccgagaaa  16260
gcccccacgc ccccaccccg cgccatcatt cccgaatctg ccctcggccc ctccccgcag  16320
cacgctcgca ggcggcacat gtcaaccaaa acgccatttc caccttctct tcccacacgc  16380
agtcctcttt tcccagggct cccccgagga gggacccacc ccaaaccccg ccattccgtc  16440
ctccctgccg ccctcgcgtg acgtaaagcc gaacccggga aactggccgc ccccgcctgc  16500
ggggttccct gggcccggcc gctctagaac tagtggatcc caattgaagg cctggtctaa  16560
atgactccaa aatcaccact taattcaaga gactgatttc cctgagtcag gccccttaaa  16620
gcagctattt caatgggaca gggaaacaac cctaggatct ggattagaat cacttggggg  16680
ctgccacacc cccagggctc tgatcctgcc cttctcccac acgcacattc acatactgct  16740
gcagtgacct tccatttcta atgggttcct gggccatctg tcaggtatag ggaatggaaa  16800
aggggttggg gaggctctgc ttcagaaagt ttgtgtcagg ggctcccaga gcctccacag  16860
atagatagca ggggtcccca ccctaccatg gcagctataa atgtgatcaa catttattgg  16920
cctaggatac agcagttagc aaaatgcctg atgtagttcc cactccgtgg aggttgcagg  16980
ctagccaaga agtcatgagt tcagcaaccc ttacgcacca gtgggatgag attggaccag  17040
gccgagggta gtcttgggaa cactcagcat ttgtctgagg gccagaagag gctgcttgcc  17100
ctcagacagg aggtcagcat ctttattgta gcccatgaca cctctacacc attgctcttc  17160
tggtcttatg gaagacatct ttgggcctga taacagcgga gtctgtgtcc cacttgtcca  17220
ggctggagtg ccacatcagg cacactccag ttgcagggac agcacagaca agtttcagga  17280
aggctggtgg cctccaggag gttaacctta taaggccaga ttgtaaccta gttgaaaaac  17340
atacacatgc catgataata aaagaaccta ggcaccatta caagagaaaa aatcattttt  17400
gtagatacga gcatggattc ttgggtgggt cagacacact gggcttgtgc tctgactgca  17460
ctgtctcccc tacctgacct tgggtaaacc ataagactgc tgcatgactc agtgtccacc  17520
ccaaaaaagt accggtagat attggccaca gtagatatca gctagagtgg actctcatga  17580
caatgagggg agatgtattc cccatcttag gcacctggga ctctaccttc catcttctgc  17640
```

-continued

```
tccgtgtctc tccatcccca ggctcttcag aactcaggga gtccagaatg tcagctccca  17700
gatttcagcc ttcagaaagg aaacccatta ccgttcagtt gaacaaatgt tgtctgagcc  17760
ccagatctgg gctcagaggc catctaggct atgagacaag aggggaacaa agcaccgtct  17820
gcactcactc accacactca cttgctgtcc caggtcacat ccatcgggta gagaatctaa  17880
gaggctgagc tagctcccgc caccagccca gcccacccca cctggcccct tccttccttc  17940
tacaaaatat gcaccacctg tcaaagggtg ggcagtgcca ggcctgcata cagagcactg  18000
agtgtaaaag cagacatgga ccctgacctc caggagcttc caattttctt gaagagacaa  18060
atcagctggc atttcagtcc agtgtgatct gctcttggtg agcacagacc tagggagttg  18120
gggcagcttc ccagaagaac tgcagtccag gctgagggca gagaaatgag gggaatggcg  18180
aggaattggg gagcaggggg gagctcagta gagagccaag ggcgggaggt gagaagtccg  18240
tgttgggcca ggagctaccc tccggtggcc acagccgaag tcgaggatgc ctttggaact  18300
catccccact tctctctttc tgtatgtagc cgtccaagaa caagtcacct ccaagtgtag  18360
ccggatcaag gcaagccccc catctagcaa gcacttgatg ccacccagaa ctgggcttct  18420
tcagaacaat ctgagtccag gaatgatccc actcaccagg caccagagct gcgagggcat  18480
gggagtgatc tcaccaactc tggggaagcg gcaaggaatt ttcacctcca gcccccagtg  18540
tcccatcctc tcacactcag gccagactcc cctgggcaga cttgactctg tctgccagca  18600
tatgcagagc cccaaggcca ccccaccaga agtgcccctg cctgggttct gtcccagctc  18660
cctgggcacc cagtccttga gtccccacca gctcagacgg cctagtgtgc caagaatgcc  18720
cactgcgttc aacaatgctg catgggtcac agcggcagca gctgtgacca cagcagtttc  18780
ggggaaaaca cccctcagcc aagtggataa tagcgttcag cagcactcac cttctggcca  18840
ggcctgcctt cagaggccat ctgattggga ggcacaagtg cccgctgcga tgggaacaca  18900
agtgcccctg gccaacaacc ccagcttcag cctgctgggc agccagagcc tcaggcagag  18960
cccggtacag ggcccggtgc ctgtagcaaa caccaccaag ttcctccagc agggtatggc  19020
cagctttagt cccctgagcc ccatacaggg catcgagcca ccaagctatg tggctgctgc  19080
tgccaccgct gctgctgctt ctgccgttgc tgccagccag ttcccaggtc cgttcgacag  19140
aacggatatt ccccctgagc tgccacctgc cgactttttg cgccagcccc aaccccccact  19200
aaatgatctg atttcgtcac ctgactgcaa tgaggtagat ttcattgaag ctctcttgaa  19260
aggctcctgt gtgagcccag atgaagactg ggtgtgcaac ttgaggctga tcgacgacat  19320
tttggaacag catgctgctg ctcaaaatgc cacagcccag aattctgggc aagtcaccca  19380
ggatgctggg gcactttaaa tctgagcagg atgcccatag aaacccccat ggtgacatca  19440
ctctaggaag tggtgtcgat ccatacccgc agttgtctcc cgttacaatt tgagtggtgt  19500
tgtcagccca tgcttatccc tctctctacc tgtgacaaaa tggaaagctg gtgatttttc  19560
aagctacgtg tacatatttg aaaattttgt aaatggtttt cctaaacatt aatgacagaa  19620
gtatttatac ttcattttgt gactttgtaa ataaagcgac ggcttttgtt tcagtagagt  19680
tgtgtttact atgcattgtt ttgtgtttat tatacaatgt tacaaatatg cagaccgtgt  19740
tgtttgctcc agtgatacct tgttaagcta ggtggctgag tcgcttatgg ttttaatgca  19800
atgagcaatg tggatatgac caagagttgt tgtgcaagtt gacaaatgcc aaatagaaaa  19860
ccacttggcc atttatttct atgttcacta aaaatcctat tgccttgtgt gattcttaat  19920
ctcttttgcg aacctttcag tctccgctag ctctttccta atgagcttta cagcagaagc  19980
```

-continued

```
tgttttatcg ttaagtgccc cacagagaca ctttaccagg aggctgggag agttctccag  20040
atttgggaga ggcgcagaga cagtgtgtga gccgagccct gtctcagcaa tccacctgga  20100
ggagctagag tatcctcctc cctttaccat tcagaccgag agaaaaagcc cagcttgtgt  20160
gcaccctcgt ggggttaagg cgagctgttc ctggtttaaa gcctttcagt atttgttttg  20220
atgtaaggct ctgtggtttg ggggggaaca tctgtaaaca ttattagttg atttggggtt  20280
tgtctttgat ggtttctatc tgcaattatc gtcatgtata tttaagtgtc tgttatagaa  20340
aacccacacc cactgtcctg taaacttttc tcagtgtcca gactttctgt aatcacattt  20400
taattgccac ctcgtatttc acctctacat ttgaaatctg gcgtctgttt caagccagtg  20460
tgtttttct tcgttctgta ataaacagcc aggagaaaag tgcctctatg tttttatttt  20520
tcaagggagt attcagtacc tacaaaccca agtcaggaag cctgctagtg gctttggttc  20580
tttcagaggc tgctcgatgc cttgtgtgtc agaaagaaag attcagcagt tttgcatcat  20640
ggcaaagaag cctgttattt tggggctcag cccctcattt tatagaggat gaaacagagg  20700
gggatgggag gtcacaaaga caactgcccc gggagcaggt gtgggggaga cttgccctga  20760
gggtctagac gctctgcacc accgtcctgt ctcccttgct gaagaccaca catgcccttc  20820
tttgaccaga ccctgccacc tgataggcca ggacctggta ggcgggtacc caggtttcat  20880
ggatggaacc acatctcccc aaaagtgggg aggtagctac tgggatgcac gcctcccgcc  20940
atgtgctata ggagagcagc tgaagcaaca gttgggatca gatgtagtca caattgaatg  21000
catcatcaca tttatccctc taagtggctg ggagagttga tatcctcatc cctaaggtac  21060
aaaatgttcc aatttgatca gtggctttca ggagctgaga aaggcatgtg ctctgaggca  21120
gagctgttat gtcccgcaga gcctaaaaat gctctaagaa catgctccct gccaaaattc  21180
tcaatggctg tgacaaggga caacgatcga ccaatggggg tggaagcaga cctccgcagt  21240
ccaggggcca gagctaggac agaggggtcg gagaaagagt cattttccca acactccagc  21300
tcttggccag tcctcacaca gtcccctcct gcttcctgct gagagagata tcctcatagg  21360
tctgggtaaa gtccttcagt cagctttcat tccctgtcac caactttgtc tctgttctcc  21420
ctgcccgtct caggcagcac tcctcaggaa acctctccaa gagccagcct cactgcagcg  21480
cccactattg tccctctgcc tcaagtgtcc catccatgcc aggccccagg caggctgcag  21540
ctttccctca gggccacacc aaagcacttg ggctcagctg tgctgtcccc ctccatcact  21600
gagctcaggg gcagcagggg tggggtgcca ggaggcccat tcacccttct ctggctctgt  21660
gttggaccca cctgcccagc cactgctgct tagaacctac ccgctgggaa aatgaagccc  21720
tcccggaggg gccacctcaa cctgagagcc tcacggatca cagttgtccc cactcagctc  21780
tgccagccct cagagaccca tagataaaag ctgagcttgg ctcgcagagc tggttccatc  21840
ttccattccc agagggttca acttcctacc ccaaccacac agggaacctc aaggctgagc  21900
cagtgtgggc tgcagtgcag accagcttcc tggacacgtc ctgccacctg accccaggct  21960
ggcctcactg cccctggcac tcctgaccct atcctcattc ctcctggcag tgcgtgttct  22020
gccattccgc tttcccttag ctgtcctctc actgtactgt cagcttctcc ttttccaggt  22080
gccccccagg ggctttccac atgaccctgt caccccacag cccatccagc accaattcca  22140
gctctctgcc acccttcaaa ggagtgacag tgccctgctt cacctcccac tcacccctca  22200
acccagagca atctggctcc agtcttgcct ccttccccct aagtactcta gtcacagttc  22260
caaattcctc ctggtcataa agccaaatga agcttcctgg tcctcagcgg acttgccact  22320
tcagcagtac tggactctct cctcccagaa acctgtttcc ccttggctcc tggagcccac  22380
```

-continued

```
actctgctgg aatccttctg cctctctggc ctgtagcctg gccctctctc ccaacctgag  22440
gtccattctc tcctgctcct ccacaagatg ttgctccttc cattacttcc tccctctcaa  22500
ccaaagctcc ttcattagct ctttatcttc tggtttcttc ccctgggcag acgaatggat  22560
tcaagagcct gtggcccagc agcccagcac tccaggatct cagcacttca gcatcccagt  22620
accctagcat ctcaataccc cagcacccca gcaccatagt attccagcac cccattgtcc  22680
aagcatctca gcactccagc atcccagcac cccaacactc cagcagccca gaatctcagc  22740
accctagcac tgcagcatct caggacccca gcacttcagc atcccagcac actagtactc  22800
cagcatctcg gcaccccagc acctaggcat cccaacaccc agcaccccag cacttaagca  22860
tcccaccact acagtatctc aacactccag caccccagca ccatagtgtt ccagcacccc  22920
agcatcccaa caccccagca cttaagcatc ccaacacctc ggcatcccaa caccccagca  22980
ctgcagcatc tcagcacctt agcatcccag tgccctagca tctcaatgct ccagcacacc  23040
agtactacag tattccagca ccccagcact ccagcatctc agcactgcag cactgcagca  23100
ctccagcatc ccaaaatccc agcatcccaa caccccagca gaccagcaga ccagcatctc  23160
agcaccgcag catccaagga ctatcccagc atcccagcaa cccagcacct cagcatccca  23220
acaccccagc atttcagcat ggcaacaccc cagtacccca gcacttcagc accccagtat  23280
cccagcatct cagcgaccca gtatcacaaa acctcagcat cctagcaccc cagcacccca  23340
gcaccttagc accttagcat cccagcatct cagcgcctca gcatcttgat attctggctg  23400
aggtcagcgt ggtgtatcta gtcagggtcc taactttcac ttcgcaggga aatgctgctg  23460
gactgggtct catgttgggc tgaagctctc tagacccctt gaagacagca taaaagagct  23520
tggagacgct gggtgtcccc catggaagag ttcactctca tcctgctttg acaacagcct  23580
tctctggggt ccctcacggg cccctctttc ttactgcaag tttgtctctg agaagactgt  23640
gatgcagaag tcactcagct gcctgtggct cctgaagagc tgaaggtgga ggcctgtagg  23700
cctccctatg agaggcgcag aaaaaaccat gattgctagt ggggaggtgc tccctctaca  23760
acccactcca taatctgccc ccgcccagct ctgaggccag ccccagggga aaatgccaga  23820
tccccaggga ggtgtgtgag acctcagggg ctccctcctc ccttacagca ggctcaggcc  23880
cctgggggcc tcagggccaa ggtctgtggg taagctacta tctctcactt gtcctctagc  23940
cacaaaagcc agggagatct ggcaatggac atgaggttct gaagaagcac atatgactgg  24000
cttcctaatg cgtggttgtt cagtgattca ataaacacgc atgggccagg catggggaaa  24060
tagacaaaca tgatccccaa cctctcccag agtgaactgg gagggaggag tgttcatccc  24120
tcaggattac accagagaaa caaaccagca ggagatatat atggttttgg ggggtcaaga  24180
aagaggaaaa acctggcaag gcaagtccaa aatcatagga caggctgtca ggaagggcag  24240
cctggaacct ctcaagcagg agctgatgct gcagtccaca ggcagaattt cttcttcctc  24300
ggggaaatct cagctttgtt cttaaggcct ttcaactgat tggctgaggt ctgccccttc  24360
ccccacattc tccaggataa tcttccttac ttaaagtcaa ctattaatca cagctacaaa  24420
atcccttcac agctacacat agatcagtgt ttgattgacg aacagcccct acagcctagc  24480
caagttgaca cataaaacta accatcacag ggggacaaat gatgtaaaca catcaacaaa  24540
taaaacagta acaagttaag gtctatggaa aaaacacaga aggggcagag agaaagaaag  24600
caagaaggag agtcccagtt tgctagggct tgtgggaagt ggggagcagt tctctttagc  24660
taggatattt gggaaaggca tatctgaagg agtgatattt gagcttagat taaaagatgg  24720
```

gaaggagcaa gccatgcaaa gagctaggat gttccaagca gagacggaac agcaagtgca 24780
aatgtcagga ggaatagaag gaggctggtg ggtggggtcc agtgagcaag aggagggcag 24840
gcaggagagg ggatggggag gtgggcaggc ccagaccacc cagggccctg gagactatcc 24900
tgatccaaca agggaagcct tgagtcactt cagtgtccat gtggagaatg gacctcagac 24960
tgaatgaggg aggcagtaag gagggcctct acctccaggg cttcgccctg tggactgcgc 25020
atagacatct ccaactcaga aagtctgaac caaactttcc atagttcccc caagtctggg 25080
catcctccta ctcagtgaaa ggcagccatc acacctccct gccctgctcc cggatgcccc 25140
aaatcctctt ggtctccaag tccagaacct gagacttgtc cttgatgttt gtctttccct 25200
caccctttct gtattctggg aagatgggtt tttttccccc agatgaatct gtaaaacttc 25260
tgtgatcaca ataaaaattc tggcagtatt attttctgga acatgacaaa gtgattcaaa 25320
attatttatc tggaagacta caaaacaaga atagccagga aatttctaaa aagaaagaag 25380
aaggaggagg agaaagaagg aggaggaaaa ggaggagaag aagaaaagaa aaagaaccaa 25440
gaaagggttc tagctctacc aaatattaaa acatatcatg aagctattta aaacaatatg 25500
gttgtggata ctgaaaaaga tgtgaataaa gtggaaggaa aataaataga aatgcacatg 25560
gggattgaga ctgtgaaaaa ggcagcatct cacatcagtg agggatgttc aacacctggt 25620
gttgggaaaa ctggctagtc atttaaacca aacaactggg tcctctacct cactcctgac 25680
attaagatac atttagatga ttcaaagagt aagacagaaa aaataacacg tgaaaacact 25740
atcagaaaac aacgtgggcc aggtgtggtg ggtcacgcct gtaatcccag cactttggga 25800
ggccgaggca gacagatcac ctgaggtggg gagttcaaga ccagcctgac caacatggtg 25860
aaatcctgtc tctactaaaa atacaaaatt agctgagcgt ggtggcgcat gcctgtaatc 25920
ccagctactc aggaggccga ggcaggagaa tcacttgaac ctgggaggca gaggttgtgg 25980
tgagccgaga tcacgccatt gcactccagc ctgggcaaca agagtgaaaa tccatctaaa 26040
aaaaaaaaaa aaagccaagg tggatatttt tatagtatca gggtagatca agcttctcca 26100
atcatgacat gaaacccaga aaccataaaa gaaaagaatg ataaaattgc ccacgtaaag 26160
taaaaagctt gcacacagaa aaacaccata caggttacaa gatgagcagc aaaatcagag 26220
aaaaaacatt gcaattcagg acacacagag gctattgttc ctaatattta aaaataaaag 26280
tagtggattg tctacaaaaa gatgaagaca agaatttcag aaaaccaaat actgcatgtt 26340
ttcacttaca agtggaagct aaacactgag tacacgtgta cacaaagaat ggaaccatag 26400
gccaggcacc gtggctcacg cctgtaatcc cagtactttg cgaggccgaa gcgggcggat 26460
cacctgaggt gaggagttcg agaccatcct ggccaacatg gtgaaaccca gtctctacta 26520
aaaatacaaa aattagccgg gcgtggtggt gggtgcctgt aatcccagct actcgggagg 26580
ctgcggcagt agaatcgctt gaaccctgga ggtggacctt gcagtgagcc gagatcgcac 26640
cactgcactc cagcctgggc aacagagtga gactccatct caaaaaaaaa aaaaaggaat 26700
agaacaatag acactggggc ctacttgagg gaggagggtg aggatcaaaa acctgcctat 26760
caggtactat gcttattacc tgggtggtga aataatctgt acaccaaacc ccagtgacat 26820
gcaatttacc gatgtaacaa acctgcccat gtacccgctg aacctaaaat aaaagttgga 26880
aaaaaatata gaaattttct ttgtaatagc caaaaactgc aaacagccca ggtgtctatt 26940
agtagaatgc ataaacaaac tcgggcatgt tcatacaatg taaaactact catcaataaa 27000
aagtgatact tctcagcaat gaaaagaaac tagctactga taccagctac aacatggatg 27060
gatttcaagt gctttatgat gagagcaaga agccagacac aaaagtgtct atatatatat 27120

-continued

```
acagtatata tacgtatata tacacatata tacagtatat atatacatat acatgtatat  27180
atatactgta tatatactgt atatatatac acagtatata tatacatata tacagtgtat  27240
atatactgtg tatatataca tgtatatata ctgtgtatat atacatgtat atatactgtg  27300
tatatataca tgtatatata ctgtgtatat atacatgtat atatatgtat actgtatata  27360
tactgtatat atatatacac atatatacag tatatatata cagtatatac tgtatatata  27420
cagtatatac gtgtatatat acatatatac agtatatatg taaatataca tatatacagt  27480
atatatgtaa atatacatat atacatgtat atatatacac tatatatata catatatagt  27540
gtatatatac atatatacat gtatatattt actatatgat tccatttata taaagtgcca  27600
aaacagtcaa aaataatcta tgtggaaaaa atcaacaaag ggatcccccg ggctgcagga  27660
attcgatggc gcgccgacgt cgcatgctcc tctagactcg aggaattcgg taccccgggt  27720
tcgaaatcga taagcttgga tccggagagc tcgataacat ttaaatggat ctaccacatt  27780
tgtagaggtt ttacttgctt taaaaaacct cccacacctc cccctgaacc tgaaacataa  27840
aatgaatgca attgttgttg ttaacttgtt tattgcagct tataatggtt acaaataaag  27900
caatagcatc acaaatttca caaataaagc aatagcatca caaatttcac aaataaagca  27960
ttttttcac tgcattctag ttgtggtttg tccaaactca tcaatgtatc ttatcatgtc  28020
gagctaggat cccgcggccg cctactggtc ctcctggagg tagaacttgg tgaccatgaa  28080
ggactctttg ggcttgttgg tgaggctgac gggccggtct gcctcctgcg ccgtgcagag  28140
gaaccagcca gggcaggcgg cagactcgaa gctggtggtg gggccactgt ttgagcggat  28200
gaaggtgaag cgcttgttct cctccttgtt cttgctcagg tcagtgatgt taactgcctc  28260
caattggaac ctaatctcat caccagactt gacacaggcc aggcacagct tcctcccatg  28320
gagtcccagg aatagagcat caggctcaat gggcaccaca tctatcttct cttgtaattt  28380
agtatttgat tcttgcaagt atccagcaac tagttggtta ttcctcatgt agaaggtctt  28440
ctggttaaca tcccagattc tgaaggcttg catcttgcag ggtctcttcc ccaaagggtg  28500
gcaggctgtc tctgagtaga gcaagaaaag gaggagagag attaggtgtc tgacagaacg  28560
cctgcggatt tccataccgg tggatccatg gctctgtctc aggtcagtat aggagctttg  28620
atgtgaagtc agccaagaac agctgaacac tacttcctct gaggcccttt tataggaggg  28680
attgcttcct gtgaataata ggaggatatt gtccacatcc agtaaagagg aaatccccaa  28740
ctgcatccaa aaagttttct gggaatatcc actgctgcag gagtggaaag tccccagtgg  28800
aaagtcccca gtggaaagtc cccagtggaa agtccccagt ggaaagtccc cagaatttcg  28860
acggcgcgcc taccagtaaa aaagaaaacc tattaaaaaa acaccactcg acacggcacc  28920
agctcaatca gtcacagtgt aaaaaagggc caagtgcaga gcgagtatat ataggactaa  28980
aaaatgacgt aacggttaaa gtccacaaaa aacacccaga aaaccgcacg cgaacctacg  29040
cccagaaacg aaagccaaaa aacccacaac ttcctcaaat cgtcacttcc gttttcccac  29100
gttacgtcac ttcccatttt aagaaaacta caattcccaa cacatacaag ttactccgcc  29160
ctaaaaccta cgtcacccgc cccgttccca cgccccgcgc cacgtcacaa actccacccc  29220
ctcattatca tattggcttc aatccaaaat aaggtatatt attgatgatg ttt         29273
```

ADENOVIRAL-BASED BIOLOGICAL DELIVERY AND EXPRESSION SYSTEM FOR USE IN THE TREATMENT OF OSTEOARTHRITIS

CROSS REFERENCE TO RELATED APPLICATIONS

This is a national stage filing in accordance with 35 U.S.C. § 371 of PCT/IB2013/000198, filed Jan. 23, 2013, which claims the benefit of the priority of European Patent Application No. 12000703.4, filed Feb. 2, 2012, the contents of each are incorporated herein by reference.

FIELD OF THE INVENTION

The invention relates to the field of genetic engineering and provides an adenoviral-based biological delivery and expression system for use in the treatment of osteoarthritis in human or mammalian joints by long-term gene expression of human or mammalian interleukin-1 receptor antagonist (Il-1Ra) in synovial cells.

DESCRIPTION OF THE BACKGROUND ART

Osteoarthrttis (OA) is a degenerative joint disease that occurs in human or mammalian joints and constitutes a severe economical and medical problem (Matthews, G. L., and Hunter, D. J. (2011). Emerging drugs for osteoarthritis. Expert Opin. Emerging Drugs 1-13.; Brooks P M. Impact of osteoarthritis on individuals and society: how much disability? Social consequences and health economic implications. Curr Opin Rheumatol 2002; 14: 573-577). Cartilage is the tough connective tissue that covers the ends of bones in joints. It provides for a relatively frictionless, highly lubricated surface between rigid bones and allows for a smooth movement. During OA development, cartilage is partially or completely lost due to abnormal or excessive wearing, which leads to exposed bone ends that rub against each other resulting in inflammation, pain, swelling or loss of mobility. By now, the detailed reasons for the initial cartilage loss that leads to OA are not known, but there is a strong correlation between the incidence and age, obesity and joint overuse such as excessive athletic activity. Accordingly, OA is a major problem not only in humans, but in many mammals, in particular in horses that join in racings and show jumping.

Especially in horses, OA constitutes a significant problem with a tremendous economic impact, Horses spend almost their entire life on their legs, and those used for athletic purposes additionally undergo excessive training. Consequently, most of the joints in athletic horses are heavily overused which often results in lameness. Lameness accounts for about 70% of the cases where horses cannot participate in races or show jumping. About 60% of the cases can be directly linked to OA (Caron J P, Genovese, R L. Principals and practices of joint disease treatment. In: Ross M W And Dyson S, eds. Diagnosis and Management of Lameness in the Horse. 1st ed. Philadelphia: Saunders, 2003:746-764). Therefore, OA is the most common reason for the inability of a horse to participate in racing competitions or shows.

No curative treatment is currently available for OA—neither for horses, humans nor for any other mammalian species. Medical treatment is mostly aimed at alleviating the symptoms using analgesic drugs rather than establishing worn away cartilage. An analgesic treatment usually involves steroids and non-steroidal anti-inflammatory drugs (NSAIDS), which have shown efficacy in the treatment of OA for some decades. However, while these drugs can suppress joint inflammation, many of them are known to have deteriorating effects on the cartilage, which further worsens the underlying process of OA development. Hyaluronic acid, for instance, which restores viscoelasticity and lubrication of the joints, has also been widely used. Furthermore, polysulphated glycosaminoglycans injected into the joint or intramuscularly as well as orally administered glucosamine and chondroitin sulphate have shown some efficacy, however their mechanisms of action are not fully understood. Thus, currently used therapies have only limited efficacy in the treatment of OA and their success often depends on the severity of the case. Moreover, these drugs must be administered frequently, sometimes even in combination with each other. However, frequent drug injections into the joint are laborious, bear the risk for infections, cause stress for the horse and are costly. In addition, surgery has generally shown low efficacy in horses and is typically only performed in severe advanced-stage subjects. It follows that there is a clear and yet unmet medical need for more efficacious and sustained treatments that are at the same time also cost effective in the long run.

During OA, interleukin-1 (Il-1) functions as a central mediator of inflammation (Dinarello C A. Interleukin-1 family. In: Thomson A W, Lotz M T (eds). The Cytokine Handbook. Academic Press: London, 2003, pp 643-668;). Moreover, Il-1 strongly inhibits matrix synthesis by cartilage and, at high concentrations, triggers matrix breakdown (Evans, C. H., Gouze, J. N., Gouze, E., Robbins, P. D., and Ghivizzani, S. C. (2004). Osteoarthritis gene therapy. Gene Ther 11, 379-389). To neutralize the effect of Il-1 on synovial inflammation, treatment with interleukin-1 receptor antagonist (Il-1Ra) constitutes a promising concept for treatment of affected osteoarthritic joints (Evans, C. H., Gouze, J. N., Gouze, E., Robbins, P. D., and Ghivizzani, S. C. (2004). Osteoarthritis gene therapy. Gene Ther 11, 379-389.; Caron J P et al. Chondroprotective effect of intraarticular injections of interleukin-1 receptor antagonist in experimental osteoarthritis. Suppression of collagenase-1 expression. Arthritis Rheum 1996; 39: 1535-1544). On nucleic acid level, Il-1Ra is considerably conserved among mammalian species. For example, the cDNA sequences of human Il-1Ra (Accession no: NM_173842) shares 82% homology with the murine variant (Accession no: NM_031167), 84% with the equine variant (Accession no: NM_001082525), 84% with the canine variant (Accession no: NM_001003096), 84% with the lapine variant (Accession no: NM_001082770) and 82% with the bovine variant (Accession no: NM_174357).

The basic concept of using gene therapy for the treatment of arthritis is well established (Evans C H, Robbins P D. Gene therapy for arthritis, In: Wolff J A (ed.). Gene Therapeutics: Methods and Applications of Direct Gene Transferm. Birkhauser: Boston, 1994, pp 320-343). In the closest prior art, the treatment of equine osteoarthritis by in vivo delivery of the equine interleukin-1 receptor antagonist gene using an adenoviral-mediated gene transfer has been described (D. D. Frisbie, S. C. Ghivizzani, P. D. Robbins, C. H. Evans, C. W. Mcllwraith, Gene Ther 9, 12-20 (2002). The adenoviral vector used for expression of equine Il-1Ra DNA was a first-generation adenoviral vector, which was shown to produce biologically active equine Il-1Ra. Although clinical examinations of the horses in this study indicated that the therapeutic expression of Il-1Ra significantly decreased signs of joint pain as measured by the degree of lameness, the effect of delivery and expression of biologically active equine Il-1Ra transgene was only short-term. Already 30 days following treatment of horses with equine Il-1Ra by intra-articular injection of various amounts of the vector bearing Il1-Ra, expression of equine Il-1Ra in joints dropped to normal levels. Similar results were also detected in the US 2003/0091536 A1, which describes adenovirus particles encoding an interleukin-1 receptor antagonist for use in the treatment of joint disease. The adenovirus particles used were first generation adenoviral vectors.

A 2-component expression system consisting of C3-human immunodeficiency virus/transactivator of transcription [C3-Tat/HIV] with the constitutive cytomegalovirus (CMV) promoter in a polyarticular collagen-induced arthritis (CIA) model in mice has been described (BAKKER A C ET AL: "C3-Tat/HIV-regulated intraarticular human interleukin-1 receptor antagonist gene therapy results in efficient inhibition of collagen-induced arthritis superior to cytomegalovirus-regulated expression of the same transgene.", ARTHRITIS AND RHEUMATISM June 2002 LNKD-PUBMED: 12115199, vol. 46, no. 6. June 2002 (2002-6), pages 1661-1670). This document specifically refers to rheumatoid arthritis (RA) as a chronic progressive autoimmune disease. It shows that collagen-induced arthritis (CIA) can be inhibited with high-systemic dosis of Il-1Ra or with local production of Il-1Ra using an ex-vivo approach.

Helper-dependent adenoviruses (HDAd), also known as gutless or high-capacity adenoviruses, are the latest generation of adenoviral vectors (Mitani, K., Graham, F. L., Caskey, C. T. & Kochanek, S. Rescue, propagation, and partial purification of a helper virus-dependent adenovirus vector. Proc Natl Acad Sci USA 92, 3854-3858 (1995); Parks, R. J. et al. A Helper-dependent adenovirus vector system: removal of helper virus by Cre-mediated excision of the viral packaging signal. Proc Natl Acad Sd USA 93, 13565-13570 (1996); Parks, R. J. Improvements in adenoviral vector technology: overcoming barriers for gene therapy. Clin. Genet. 58, 1-11 (2000)). These vectors are devoid of all viral sequences and are able to mediate long-term gene expression in various tissues (e.g. 7 years in the liver) in contrast to the more immunogenic first generation adenoviruses (Brunetti-Pierri, N. at a Multi-Year Transgene Expression in Nonhuman Primates Following Hepatic Transduction with Helper-Dependent Adenoviral Vectors. American Society of Gene & Cell Therapy, Annual Meeting 2011 Molecular Therapy Volume 19, Supplement 1, May 2011). However, longevity of helper-dependent adenoviruses mediated gene expression in joints has not been evaluated to date.

Further helper-dependent adenoviral vector systems and their generation have also been described (PALMER DONNA ET AL: "Improved system for helper-dependent adenoviral vector production.", MOLECULAR THERAPY: THE JOURNAL OF THE AMERICAN SOCIETY OF GENE THERAPY November 2003 LNKD-PUBMED: 14599819, vol. 8, no. 5, November 2003 (2003-11), pages 846-852, TOILEATTA GABRIELLE ET AL: "Generation of helper-dependent adenoviral vectors by homologous recombination.", MOLECULAR THERAPY: THE JOURNAL OF THE AMERICAN SOCIETY OF GENE THERAPY February 2002 LNKD-PUBMED: 11829528, vol. 5, no. 2, February 2002 (2002-02), pages 204-210).

The U.S. Pat. No. 5,747,072 A describes and claims a recombinant adenoviral vector having an expression control sequence operatively linked to a gene that encodes an anti-inflammatory polypeptide, ribozyme or antisense RNA molecule. Administering to the joint a therapeutically effect amount of a recombinant first generation adenoviral vector resulted in a reduced inflammatory response in the joint of the treated subject. Again, as in other studies, the long-term expression of Il-1Ra was limited.

SUMMARY OF THE INVENTION

It is therefore an object of the present invention to provide an improved delivery and expression system that allows for a long-term expression of biologically active recombinant interleukin-1 receptor antagonist (Il-1Ra) in synovial cells at human or mammalian joints for treatment and prevention of osteoarthritis. The solution for the problem is provided by an adenoviral-based biological delivery and expression system having the features as claimed in claim 1. Preferred embodiments of the invention are subject-matter of the dependent claims.

The adenoviral-based biological delivery and expression system according to the present invention is based on a helper-dependent adenoviral vector containing a nucleic acid sequence encoding for human or mammalian interleukin-1 receptor antagonist (Il-1Ra), left and right inverted terminal repeats (L ITR and R ITR), adenoviral packaging signal and non-viral, non-coding stuffer nucleic acid sequences. Furthermore, the gene of the human or mammalian interleukin-1 receptor antagonist (Il-1Ra) is controlled by an inflammation-inducible promoter. Preferred inflammation-regulated promoters for use in the present invention are NF-κB promoter, intedeukin 6 (Il-6) promoter, interleukin-1 (Il-1) promoter, tumor necrosis factor (TNF) promoter, cyclooxygenase 2 (COX-2) promoter, complement factor 3 (C3) promoter, serum amyloid A3 (SAA3) promoter, macrophage inflammatory protein-1α (MIP-1α) promoter, or hybrid constructs of the above. The promoter sequences are upstream of the reading frame of the cloned Il-1Ra gene. The inflammation-regulated promoter according to the present invention is specifically activated by increased levels of immune stimulatory substances such as lipopolysaccharide (LPS), which is a major component of the outer cell membrane of gram-negative bacteria. During osteoarthritis, a variety of immune stimulatory substances and cytokines are released, resulting in high levels of promoter-activating substances. One component, for instance, is NF-κB, which regulates the NF-κB promoter. Therefore, the release of such osteoarthritic-specific activators allows for the control of gene expression in joints of humans or mammals for treating or preventing an osteoarthritic condition.

The use of an inflammation-inducible promoter provides for specific control of Il-1Ra gene expression in osteoarthritic tissue cells. Only cells that are affected by the disease will express and secrete the Il-1Ra gene product, whereas cells that are not affected remain silent. The use of NF-κB5-ELAM promoter for inflammation-dependent gene expression is most preferred. However, any other inflammation-dependent promoter that result in a specific expression of the Il-1Ra gene product in osteoarthritic tissue can be used in context of the present invention.

The helper-dependent adenoviral vector as used in the present invention minimizes immune responses in the host, and confers long-term gene expression of human or mammalian Il-1Ra in joints that are affected by osteoarthritis.

To be most effective, the helper-dependent adenoviral vector of the invention is preferably administered in a single injection dose directly into the joints of the osteoarthritic subjects. Following intra-articular injection, the gene of Il-1Ra is delivered to synovial cells such as synoviocytes. Synovial cells that are affected by inflammation start to produce recombinant Il-1Ra protein under the control of the inflammation-inducible promoter such as the NF-κB promoter. High amounts of Il-1Ra are then secreted into the joint space, where Il-1Ra is able to inhibit inflammation and stop cartilage degradation by blocking the interleukin-1 receptor on the surface of synoviocytes and the cells embedded in the cartilage. Most importantly, high local concentrations of recombinant Il-1Ra do not show any side effects.

Therefore, as shown in the examples below, pain, inflammation and cartilage degradation are inhibited effectively using the adenoviral-based biological delivery and expression system according to the present invention. High local and low systemic concentrations of the therapeutic protein Il-1Ra are achieved, resulting in maximum efficacy in the treatment of OA at no or minimal side effects. It is further exemplified that cells containing the helper-dependent adenoviral vector of the invention are capable to produce recombinant Il-1Ra for an extended period of at least one year. Consequently, medical and economic burden associated with frequent joint injections that were required in the known short-term treatments will be significantly reduced. In particular, the serious long-term side effects of commonly used steroids can be avoided by using the helper-dependent adenoviral vector of the invention due to its cartilage protective effect. Thus, common complications associated with OA treatment are minimized and joint health will be preserved in the long run resulting in sustained health improvement of the treated animal or human.

In addition, the inflammation-dependent Il-1Ra production of the vector of the invention allows for the prevention of the development of an osteoarthritic condition as synovial cells that are infected with the adenoviral vector of the invention remain silent in the absence of immune stimulatory substances that could activate the NF-κB5-ELAM promoter or any other inflammation-dependent promoter. Only if the osteoarthritic condition initiates, the promoter is activated as a result of inflammation and subsequently Il-1Ra is produced and secreted. Thus, by using the adenoviral delivery and expression system of the invention, this mechanism allows for the prevention of the development of osteoarthritis in an early stage.

An inflammation-dependent Il-1Ra production of the vector of the invention can also be viewed as a safety feature to ensure that Il-1Ra is no longer produced, for example when the osteoarthritic condition is resolved or has disappeared.

The helper-dependent adenoviral vector as used in the present invention does not carry any viral sequences, except the left and right inverted terminal repeats (ITRs) and the adenoviral packaging signal. Preferred helper-dependent adenoviral vectors to be used in the present invention are those based on the helper virus and helper-dependent backbone system developed by Palmer and Ng (Palmer, D., and Ng, P. (2003). Improved system for helper-dependent adenoviral vector production. Mol Ther 8, 846-852.) and Toietta et al (Toietta, G., Pastore, L., Cerulo, V., Finegold, M., Beaudet, A. L., and Lee, B. (2002). Generation of helper-dependent adenoviral vectors by homologous recombination. Mol Ther 5, 204-210.). A preferred adenoviral delivery and expression system according to the present invention comprises a nucleic acid sequens set forth in SEQ ID NO 2 or SEQ ID NO3, or a biologically effective part thereof. The nucleic acid sequence of SEQ ID NO 2 describes a murine helper-dependent adenoviral vector, and the sequence set forth in SEQ ID NO 3 describes a equine helper-dependent adenoviral vector, both bearing the murine and equine Il-1Ra gene, respectively. Preferably, the system of the invention has at least 50%, 60%, 70%, 80%, 90% sequence homology with the vector set forth in SEQ ID NO 2 or SEQ ID NO 3.

"Biologically effective" in the context of the present invention means that the gene product of the adenoviral delivery and expression system comprises the full or partial polypeptide sequence of Il-1Ra having the in-joint activity to neutralize the effect of Il-1 on synovial inflammation.

The helper-dependent adenoviral vector of the invention preferably contains the cDNA sequence of Il-1Ra that is controlled by the inflammation-inducible promoter. Although Il-1Ra contains species-specific nucleic acid sequences, the adenoviral vector is able to express interleukin-1 receptor antagonist (Il-1Ra) from any mammalian species or human. Preferably, the cDNA of the mammalian interleukin-1 receptor antagonist (Il-1Ra) used for cloning is a cDNA selected from the group consisting of murine Il-1Ra, equine 1-1Ra, canine Il-1Ra, cat Il-1Ra, rabbit Il-1Ra, hamster Il-1Ra, bovine Il-1Ra, camel Il-1Ra or their homologs in other mammalian species.

In order to monitor the presence of genomic vector sequences in synovial cells, the helper-dependent adenoviral vector according to the invention preferably further comprises a marker gene that is visually or instrumentally detectable. Preferred marker genes are, for instance, green fluorescence protein (GFP) or luciferase enzyme.

As an example, the nucleic acid sequence of murine Il-1Ra as used in the present invention is shown in the sequence listing set forth in SEQ ID NO 1. As noted above, any nucleic acid sequence resulting in a biologically active Il-1Ra protein of any mammalian or human species can be used in the context of the present invention. Furthermore, also conserved nucleic acid sequences encoding for the same amino acids, polypeptide or protein fall under scope of the present invention. As illustrated in the prior art, Il-1Ra genes of various species share a high homology among each other. Preferably, the helper-dependent adenoviral vector according to the invention contains a nucleic acid sequence (e.g. cDNA) of Il-1Ra having at least 50%, 60%, 80%, 90% sequence homology with the nucleic acid sequence shown in SEQ ID NO 1. The invention also comprises biologically active nucleic acid sequences of Il1-Ra or fragments thereof beside the full-length nucleic acid sequence of Il1 Ra.

The present invention further comprises a pharmaceutical composition, comprising a helper-dependent adenoviral vector containing a nucleic acid sequence encoding for human or mammalian interleukin-1 receptor antagonist (Il-1Ra), left and right Inverted terminal repeats (L ITR and R ITR), packaging signal and non-viral, non-coding stuffer nucleic acid sequences, wherein the expression of the human or mammalian interleukin-1 receptor antagonist (Il-1Ra) gene within synovial cells is regulated by an inflammation-inducible promoter, for the treatment or prevention of osteoathritis. Preferred promoters as used in the context of the present invention are NF-κB promoter, interleukin 6 (Il-6) promoter, interleukin-1 (Il-1) promoter, tumor necrosis factor (TNF) promoter, cyclooxygenase 2 (COX-2) promoter, complement factor 3 (C3) promoter, serum amyloid A3 (SAA3) promoter, macrophage inflammatory protein-1α (MIP-1α) promoter, or hybrid constructs of the above.

It is a great benefit of the present invention that the adenoviral delivery and expression system specifically locates in the joints when administered intra-articularly. Most importantly, no measurable concentration of vector sequences could be deteced in the liver of mice treated with the adenoviral system of the invention. Therefore, Il-1Ra concentrations are expected to be highest in the joints injected with the vector of the invention while no significant side effects are expected in any other organ.

The invention will be further illustrated in the examples following below.

BRIEF DESCRIPTION OF THE DRAWINGS

Figure Legends

Figure 1:
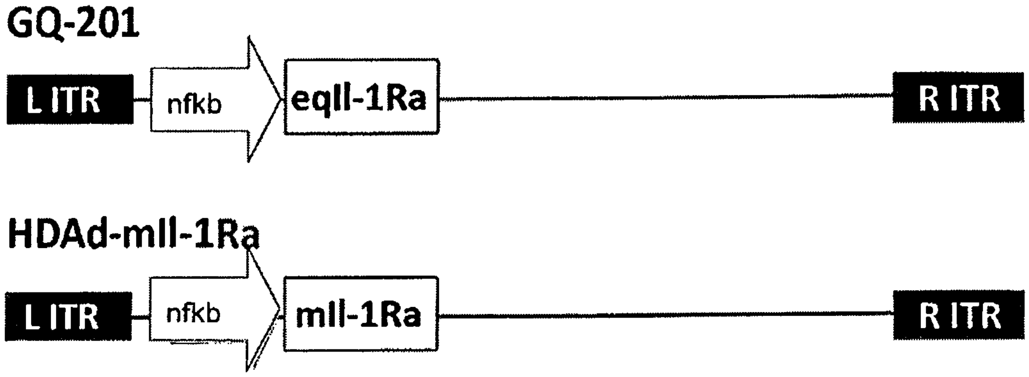
FIG. 1

The Figure shows a basic gene map of the helper-dependent adenoviral vector of the invention. The vector backbone consists of the left and right inverted terminal repeats (ITR), adenoviral packaging signal (ψ) and non-coding, non-viral stuffer sequences (remaining unmarked sequence between ITRs). The cDNA of murine Il-1Ra is cloned between the viral left and right ITRs of the used adenoviral vector. The gene of Il1-Ra is controlled by inflammation-inducible NF-κB5-ELAM promoter.

FIG. 2

A. Helper-dependent and first generation adenoviral vectors mediate the same level of marker gene expression. Mice were injected intra-articularly with $10^8$ virus particles (VP) of a luciferase expressing helper-dependent (HDAd-kuc) or a respective first generation (Ad-luc) adenoviral vector. Three days later mice were imaged using IVIS 200 series imaging system (Caliper Life Sciences, Hopkintom M A). Strong bioluminescence signals were detected in the joints injected with both HDAd-luc and Ad-luc adenoviral vector. Both knee joints of four mice per group were injected; representative pictures of two mice of each group are shown.
B. Helper-dependent adenoviral vector mediates long-term marker gene expression in joints. Luciferase expression of the mice described in A was followed by repeated bioluminescence imaging and quantified using Living Image 2.5 software (Caliper Life Sciences). Expression decreased and was undetectable by 30 days with the first generation adenoviral vector (Ad-luc). With the helper-dependent adenoviral vector (HDAd-luc) expression also declined but plateaued at 10 days and has been around this level for 380 days.

FIG. 3

Helper-dependent adenoviral vector infects synoviocytes efficiently. Mice were injected intra-articularly with $10^8$ VP of a LacZ expressing HDAd. One day later, mice were sacrificed and LacZ staining on sectioned joints was performed. Strong expression (dark blue staining) was seen in the synovium while no staining could be observed in chondrocytes. Right picture is a higher magnification photograph (40×) of the framed area in the left picture (5×).

FIG. 4

Cells infected with HDAd-Il-1Ra produce large amounts of Il-1Ra. Human embryonic kidney cells (HEK293) were infected with 100 VP/cell of HDAd-Il-1Ra, HDAd-GFP or mock. Two days later Il-1Ra ELISA was performed with cell culture supernatant. Concentrations of about 700 pg/ml were measured for HDAd-Il-1Ra infected cells, whereas no Il-1Ra was detectable in the supernatant of HDAd-GFP or mock infected cells. To induce an inflammatory reaction, lipopolysaccharides (LPS, 100 ug/ml) were added to half of the samples and Il-1Ra concentrations were again determined one day later (day 4). Levels in HDAd-Il-1Ra samples increased to about 1600 pg/ml whereas uninduced cells produced less Il-1Ra compared to the previous day. No Il-1Ra expression was detected in any of the control samples (HDAd-GFP and mock).

FIG. 5

HDAd-Il-1Ra prevents the development of OA. Mice were injected intra-articularly into the knee joints with $10^8$ VP of HDAd-Il-1Ra, HDAd-GFP or mock and OA was induced by cruciate ligament transduction two days later. Mice were sacrificed after 4 weeks and joints were histologicaly prepared, sectioned and stained with Safranin O. A blinded pathologist evaluated the level of OA according to OARSI (Osteoarthritis Research Society International) standards (assignment of scores on a scale of 1-6, 1: no signs of OA at all, 6: maximum OA). Mice treated with HDAd-Il-1Ra had significantly lower OA scores compared with mice treated with HDAd-GFP and mock. (* indicates significant difference: $p<0.05$ by one-way ANOVA; n=10 joints per group).

FIG. 6

HDAd-Il1Ra efficiently treats OA in mice.

A. HDAd-Il-1Ra treated joints have significantly lower OA scores compared to controls. OA was induced in mouse knee joints by cruciate ligament transection and the disease was allowed to develop. Two weeks after transection, mice were injected intra-articularly with $10^8$ VP of HDAd-Il-1Ra, HDAd-GFP or mock. Mice were sacrificed 6 weeks later and joints were histologically prepared, sectioned and stained with Safranin O. A blinded pathologist evaluated the level of OA according to OARSI (Osteoarthritis Research Society International) standard (assignment of scores on a scale of 1-6, 1: no signs of OA at all, 6: maximum OA). Mice treated with HDAd-Il-1Ra had significantly lower OA scores compared with mice treated with HDAd-GFP and mock. No significant difference was found between the HDAd-Il-1Ra group and age matched, untransected (no OA induction) mice. (* indicates significant difference: $p<0.05$ by one-way ANOVA; n=8 joints per group).

B. HDAd-Il-1Ra treated joints demonstrate significantly higher cartilage volume compared to controls. Whole knee joints of mice treated the same way as described above were fixed in electron microscopy fixative and embedded in paraffin. Samples were scanned using X-radia microXCT scanner (Xradia, Pleasanton, Calif., USA) and was visualized at 4 micron resolution. Computational 3D reconstruction of joints was performed and cartilage volume and surface area were quantified semi-automatically using TRI BON software (RATOC System Engineering, Tokyo, Japan). Significantly higher cartilage volume was measured in HDAd-Il-1Ra treated joints in comparison to controls. HDAd-Il-1Ra joints had similar volumes as untransected (healthy) joints. (* indicates significant difference: $p<0.05$, one-way ANOVA, n=6 joints/group).

C. HDAd-Il-1Ra treated joints demonstrate significantly larger cartilage surface area compared to controls. Cartilage surface area was measured as described above. HDAd-Il-1Ra treatment resulted in significantly higher cartilage surface area compared to controls. Surface area of HDAd-Il-1Ra treated joints was similar to that of untransected (healthy) controls. (* indicates significant difference: $p<0.05$, one-way ANOVA, n=6 joints/group).

EXAMPLES

High levels of Il-1Ra were measured in supernatants of synovial cells that were infected with a helper-dependent adenoviral vector (HDAd) of the invention. As shown below, the induction of inflammation with lipopolysaccharide (LPS) led to a dramatic increase of Il-1Ra concentration as compared with uninduced samples. NoIl-1Ra was detected in non-infected samples (mock) or samples infected with a control vector (HDAd-GFP). The experiments demonstrate that cells infected with HDAd-mIl-1Ra can produce high levels of Il-1-RA. It further shows that Il-1Ra is efficiently secreted from those cells, and that inflammatory conditions activate the NF-κB5-ELAM promoter leading to increased Il-1Ra levels.

Production of the Helper-Dependent Adenoviral Vector of the Invention

FIG. 1 shows gene maps of the HDAd vectors of the invention. The full vector sequence is shown in SEQ ID NO 2 OR SEQ ID NO 3. The only difference between the two vectors is that GQ-201 carries the equine variant of Il-1Ra whereas HDAd-mIl-1Ra has the murine Il-1Ra variant Both vectors contain the inflammation inducible NF-κB5-ELAM promoter upstream of the Il-1Ra cDNA according to SEQ ID NO 1 as well as inverted terminal repeats (ITR) and an adenoviral packaging signal. The vectors were cloned by standard digestion/ligation reactions according to the following strategy. The luciferase cDNA in pNifty-luc, a plasmid that contains the luciferase cDNA driven by a NF-κB5-ELAM promoter, was excised with NcoI and NheI and cDNAs for equine or murine Il-1Ra were ligated into this position. The NF-κB5-ELAM promoter—murine Il-1Ra or NF-κB5-ELAM promoter—equine Il-1Ra cassettes were excised with NotI and PacI or EcoRI and PacI, blunted and inserted into pLPBL shuttle plasmid, which had been linearized with SaiI and blunted. The NF-κB5-ELAM promoter—murine Il-1Ra or NF-κB5-ELAM promoter—equine Il-1Ra cassettes were then excised with AscI, which flanks both sides of the multiple cloning site, and ligated into AscI linearized pΔ28 plasmid (Toietta, G., Pastore, L., Cerullo, V., Finegold, M., Beaudet, A. L., and Lee, B. (2002). Generation of helper-dependent adenoviral vectors by homologous recombination. Mol Ther 5, 204-210.), which yielded the genomic plasmids pΔ28-mIl-1Ra and pΔ28-eqIl-1Ra. These plasmids were digested with PmeI in order to linearize the vector, liberate the inverted terminal repeats and excise bacterial resistance genes. Vectors were rescued and amplified as described before using the helper-virus AdNG163R-2 and 116 cell factories (Palmer, D., and Ng, P. (2003). Improved system for helper-dependent adenoviral vector production. Mol Ther 8, 846-852; Suzuki, M., Cela, R., Clarke, C., Bertin, T. K., Mouriño, S., and Lee, B. (2010). Large-scale production of high-quality helper-dependent adenoviral vectors using adherent cells in cell factories. Hum Gene Ther 21, 120-126.)

HDAd Mediates Long-Term Marker Gene Expression in Joints

Figure 2:
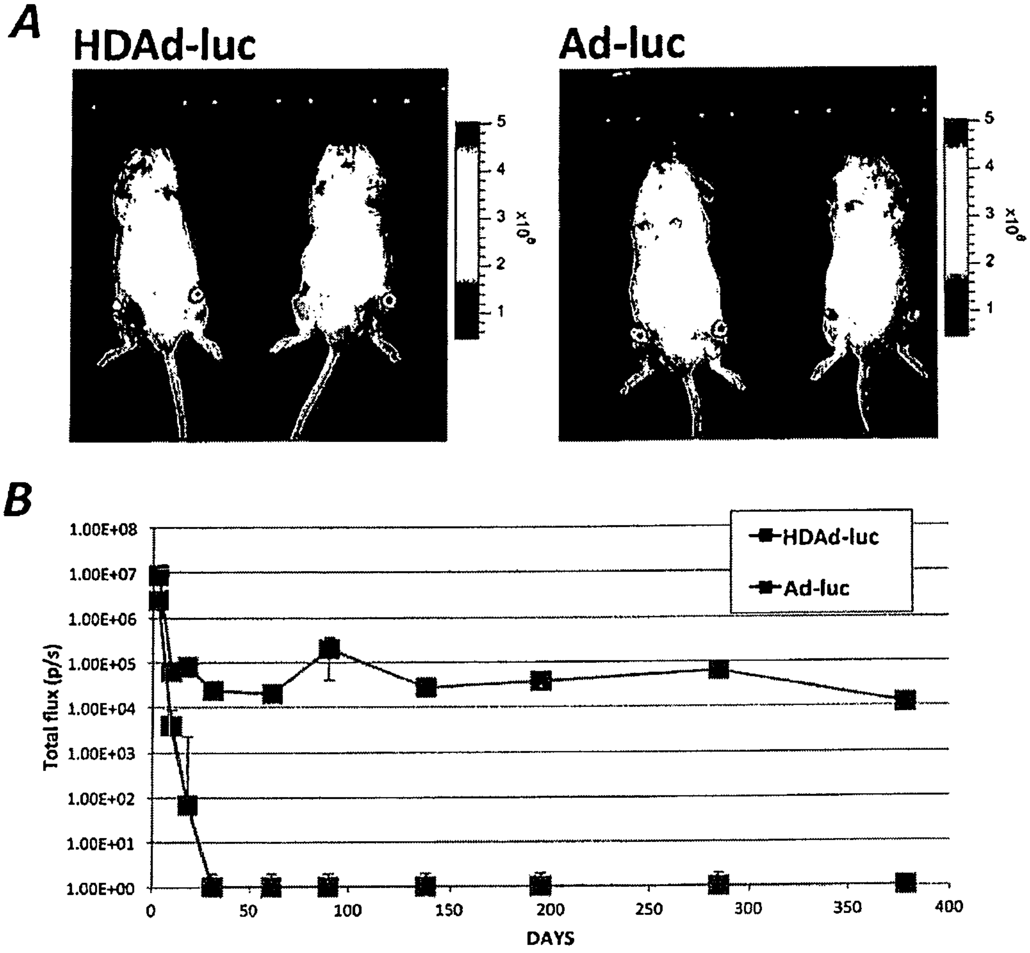

In order to determine long-term gene expression for up to one year in joints, mice were injected intra-articularly with a helper-dependent adenoviral vector of the invention (HDAd) and, for comparison, a first generation adenovirus (Ad) vector expressing firefly luciferase (luc) under the control of a CMV promoter. Luc expression was followed over time using in vivo bioluminescence imaging. Strong initial luc signals were detected three days after injection with both vectors (FIG. 2A). Expression decreased with both vectors thereafter and was undetectable after one month with the first generation vector Ad-luc (FIG. 2B). However, HDAd-luc luciferase expression stabilized at day 10 and has been at this level for 380 days.

HDAd Transduces Synovial Cells Following Intraarticular Injection

Figure 3:
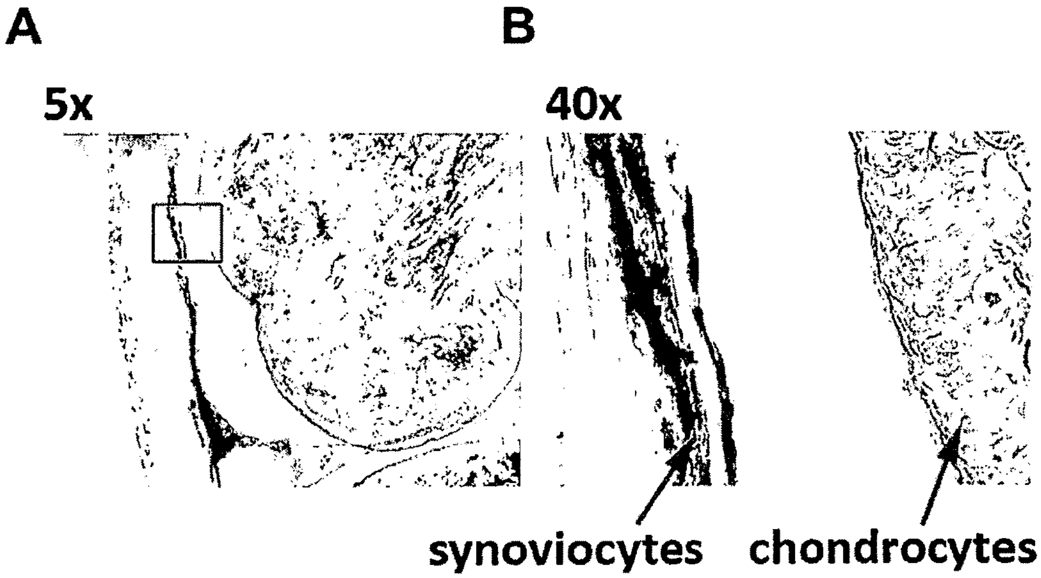

To evaluate HDAd transduction in mouse joints in detail, mice were injected intra-articularly with a LacZ expressing HDAd. Strong LacZ expression was seen in the synovium, however, no expression could be observed in chondrocytes (FIG. 3). The inventors also analyzed the liver of these animals to assess whether virus escapes from the joints or is spilled during the injection. Most importantly, no detectable vector concentrations over background could be measured by quantitative PCR (data not shown). Therefore, the vector specifically locates in the joints and remains there, which is of great benefit in the treatment or prevention of an osteoarthritic condition since it suggests minimal side effects.

HDAd-Il-1Ra Infected Cells Secrete Il-1Ra

Figure 4:
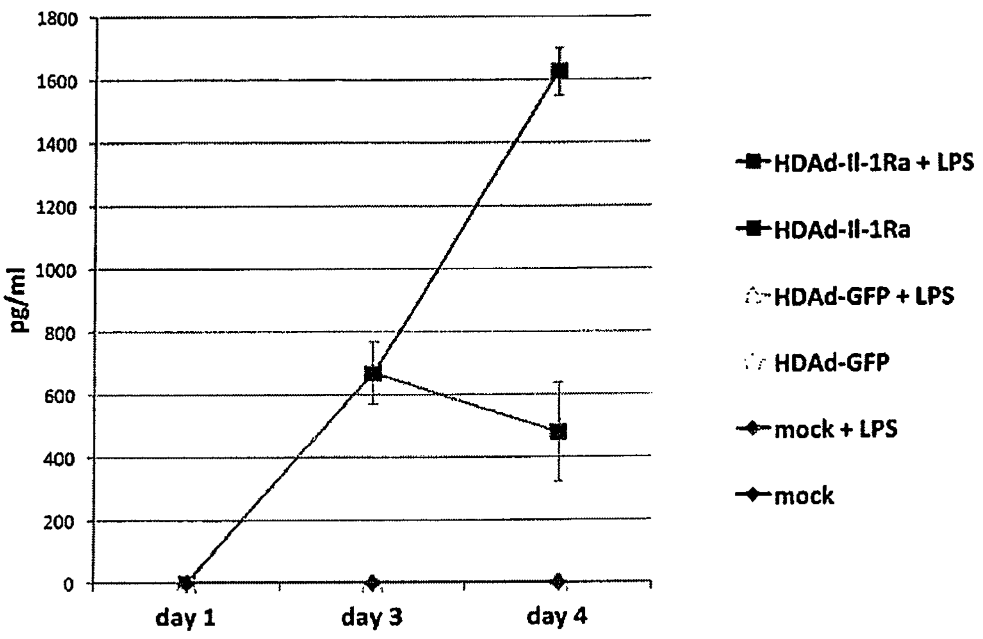

An HDAd expressing Il-1Ra under the control of the inflammation inducible NF-κB5-ELAM promoter was generated and its functionality was tested in vitro. High levels of Il-1Ra were measured in the supernatant of HDAd-Il-1Ra infected cells on day 3 (FIG. 4). Induction of inflammation with lipopolysaccharide (LPS) led to a dramatic increase of Il-1Ra concentration compared with uninduced samples. NoIl-1Ra was detected in non-infected samples (mock) or samples infected with a control vector (HDAd-GFP).

HDAd-Il-1Ra Prevents the Development of OA in Mice

Figure 5:
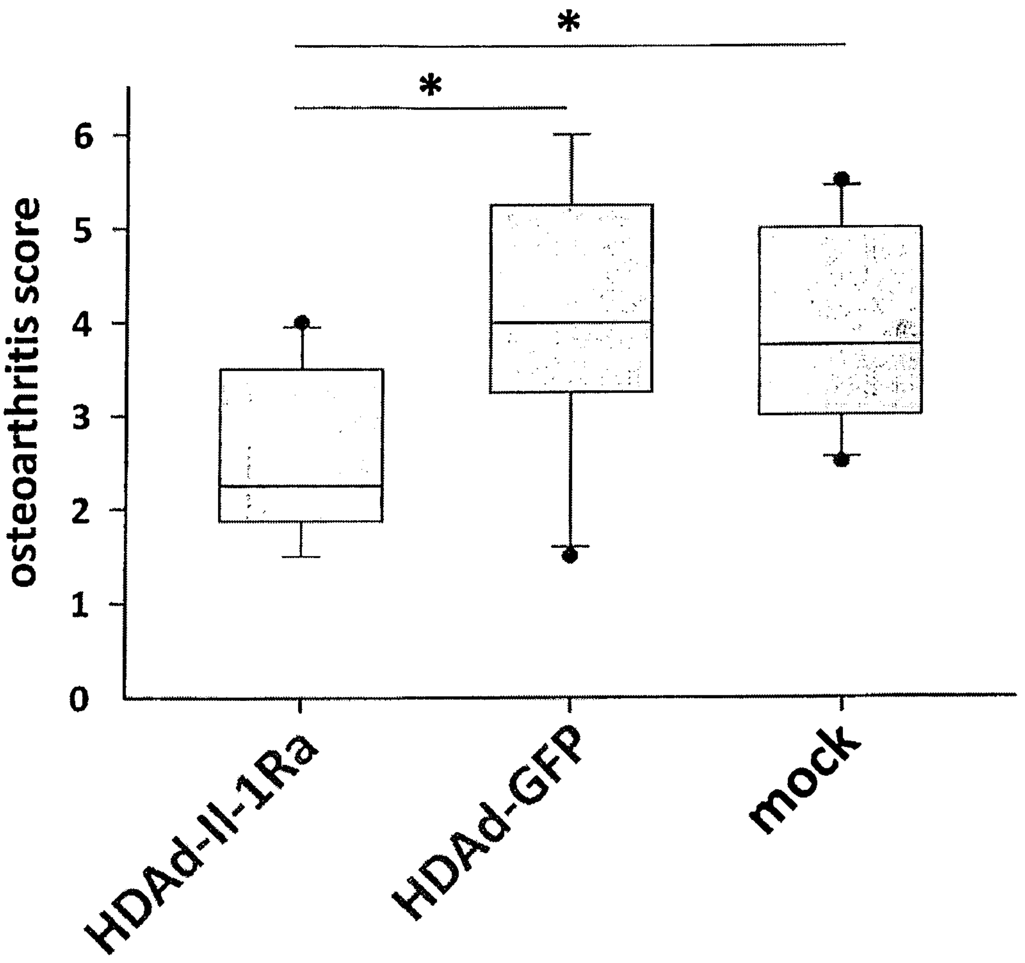

To assess whether an HDAd expressing Il-1Ra is able to prevent the development of OA, knee joints of mice were injected intra-articularly with HDAd-Il-1Ra or a GFP expressing control vector (HDAd-GFP). Two days after injection, cruciate ligament transection was performed to induce OA development This osteoarthritis model was developed in Dr. Brendan Lee's research group and validated in several experiments (Ruan, Z., Dawson, B., Jiang M. M., Gannon, F., Heggeness, M., Lee, B. (2012). Quantitative volumetric imaging of murine osteoarthritic cartilage by phase contrast micro-computed tomography, submitted). The model involves transection of anterior and posterior cruciate ligaments of the knee joints, which leads to development of severe OA. Mice were sacrificed one month after OA induction and joints were prepared histologicaly and stained with Safranin O. The development of OA was scored by a blinded pathologist according to OARSI (Osteoarthritis Research Society International) standard (assignment of scores on a scale of 1-6, 1: no signs of OA at all, 6: maximum OA). HDAd-Il-1Ra treated joints had significantly lower OA scores than HDAd-GFP treated or untreated joints, suggesting that HDAd-Il1Ra prevented the development of OA (FIG. 5). The control vector HDAd-GFP did not seem to have any effect on the development of OA since the average OA score was comparable to the score of the untreated group.

HDAd-mIl-Ra Treats OA in a Murine Model of the Disease

Figure 6:
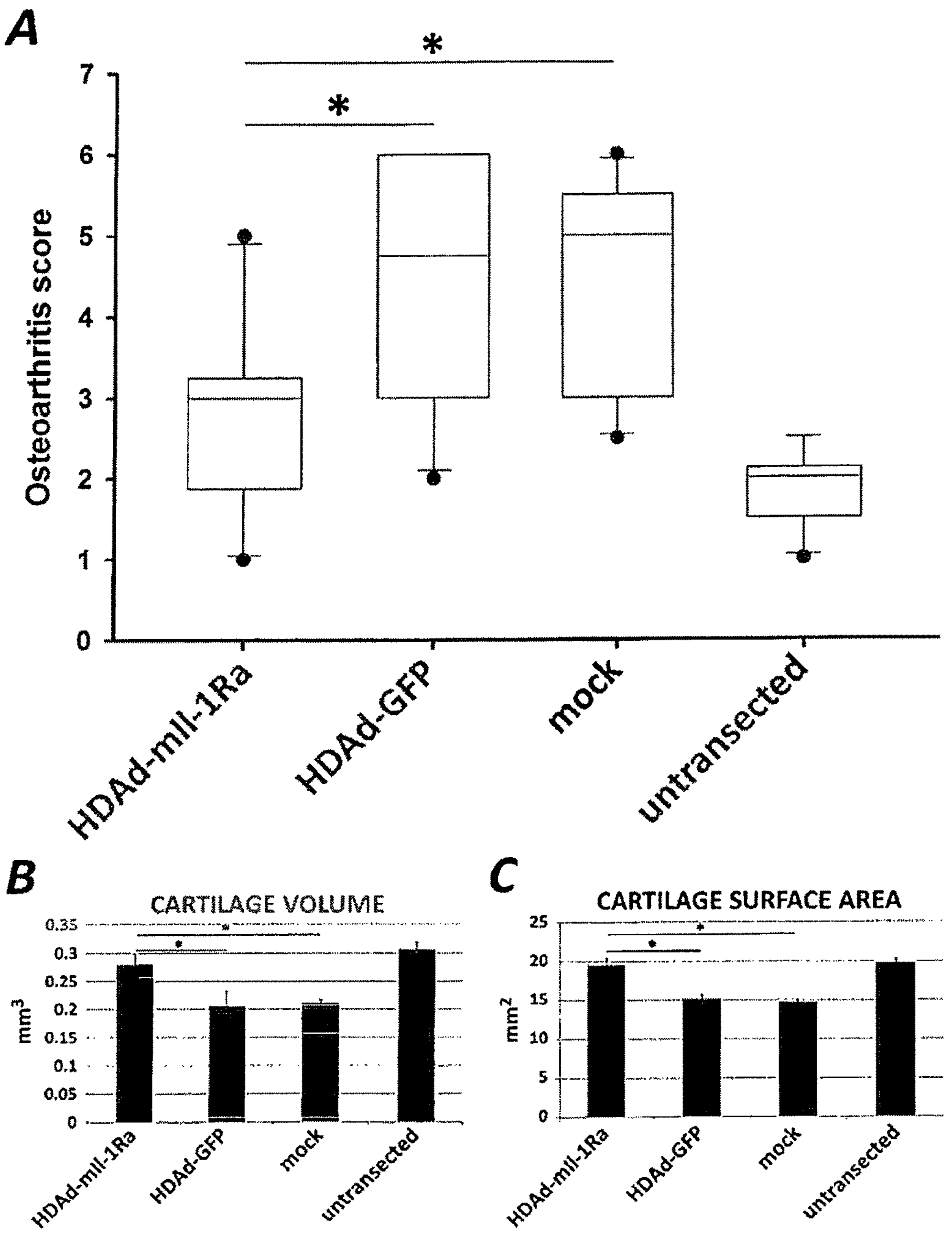

The efficacy of HDAd-mIl-1Ra in the treatment of OA was evaluated in the murine disease model described above. The model was used to assess whether HDAd-Il1-Ra can efficiently treat OA. Therefore, OA was induced by cruciate ligament transection (except in the untransected group) and OA was allowed to develop for two weeks. HDAd-Il-1Ra, the control vector (HDAd-GFP) or vehicle was then injected and mice were sacrificed to analyze the joints another six weeks later. HDAd-GFP treated and uninjected mice developed OA to the same extent with an average score of approximately 4.5 (FIG. 6A). However, HDAd-Il-1Ra treated mice had significantly lower OA scores compared with HDAd-GFP and mock treated. No significant difference was found between HDAd-Il-1Ra and untransected (OA-free) mice suggesting efficient treatment of the disease or its prevention. The inventors further evaluated the joints in this experiment by micro computer tomography (μCT) analysis. This technique combines high resolution (down to 0.5 micron) x-ray CT scanning with phase contrast optics, which enables visualization of cartilage in small animal joints. Three-dimensional reconstruction of joints and computational tissue analysis tools can be used to quantify several cartilage parameters such as volume and surface area. HDAd-Il-1Ra treated joints demonstrated significantly higher cartilage volume compared with HDAd-GFP and mock treated joints (FIG. 6B). No significant difference was seen between the HDAd-Il-1Ra and untransected (OA-free) groups. Furthermore, cartilage surface area was significantly larger in HDAd-Il-1Ra treated mice compared with HDAd-GFP and mock groups (FIG. 6C), while no significant difference was seen between HDAd-Il-1Ra and untransected (OA-free) joints.

The invention claimed is:

1. A pharmaceutical composition comprising an adenoviral-based biological delivery and expression system for the treatment of osteoarthritis or an osteoarthritic condition in a human or a mammalian joint or for the prevention of such conditions in a human or a mammalian identified to be at risk of developing osteoarthritis or an osteoarthritic condition, said adenoviral-based biological delivery and expression system comprising a helper-dependent adenoviral vector containing a nucleic acid sequence encoding a human or a mammalian interleukin-1 receptor antagonist (IL-1Ra), a left and right inverted terminal repeats, an adenoviral packaging signal and non-viral, non-coding stuffer nucleic acid sequences, wherein the expression of the human or the mammalian IL-1Ra gene is regulated by a one component inflammation-inducible promoter, which is located upstream of the reading frame of the nucleic acid sequence encoding the human or the mammalian IL-1Ra and which is specifically activated by immune stimulatory substances, wherein the inflammation-inducible promoter is an NF-kB promoter, and wherein the promoter, the left and the right inverted terminal repeats, the adenoviral packaging signal and the non-viral, non-coding stuffer nucleic acid sequences have at least 90% sequence homology to the nucleic acid sequence of SEQ ID NO: 2 or SEQ ID NO: 3.

2. The pharmaceutical composition according to claim 1, wherein the helper-dependent adenoviral vector comprises the nucleic acid sequence of SEQ ID NO: 2 or SEQ ID NO: 3.

3. The pharmaceutical composition according to claim 1, wherein the mammalian IL-1Ra is selected from the group consisting of murine IL-1Ra, equine IL-1Ra, canine IL-1Ra, cat IL-1Ra, rabbit IL-1Ra, hamster IL-1Ra, bovine IL-1Ra, camel IL-1Ra or homologs thereof in other mammalian species.

4. The pharmaceutical composition according to claim 1, wherein the helper-dependent adenoviral vector additionally comprises a marker gene encoding a protein product that is visually or instrumentally detectable to monitor the presence of the vector sequences in infected cells.

5. The pharmaceutical composition according to claim 1, wherein the IL-1Ra in the helper-dependent vector comprises the nucleic acid of SEQ ID NO 1.

6. A process of infecting joint cells of a human or a mammal suffering from osteoarthritis or an osteoarthritic condition with an adenoviral-based biological delivery and expression system comprising the steps of: infecting the joint cells of the human or the mammal suffering from the osteoarthritis or the osteoarthritic condition with the adenoviral-based biological delivery and expression system which comprises a helper-dependent adenoviral vector containing a nucleic acid sequence encoding human or mammalian IL-1Ra, left and right inverted terminal repeats, an adenoviral packaging signal and non-viral, non-coding stuffer nucleic acid sequences, wherein the expression of the human or the mammalian IL-1Ra gene is regulated by a one component inflammation-inducible promoter, which is located upstream of a reading frame of the nucleic acid sequence encoding the human or the mammalian IL-1Ra and which is specifically activated by immune stimulatory substances; and expressing IL-1Ra in the joint cells, wherein the inflammation-inducible promoter is an NF-kB promoter, and wherein the promoter, the left and the right inverted terminal repeats, the adenoviral packaging signal and the non-viral, non-coding stuffer nucleic acid sequences have at least 90% sequence homology to the nucleic acid sequence of SEQ ID NO: 2 or SEQ ID NO: 3.

7. A process of treating osteoarthritis or an osteoarthritic condition in human or mammalian joints or preventing a human or mammal identified to be at risk of developing osteoarthritis or an osteoarthritic condition in human or mammalian joints from developing an osteoarthritis or an osteoarthritic condition, the process comprising administration of an adenoviral-based biological delivery and expression system comprising a helper-dependent adenoviral vector containing a nucleic acid sequence encoding human or mammalian IL-1Ra, left and right inverted terminal repeats, an adenoviral packaging signal and non-viral, non-coding stuffer nucleic acid sequences, wherein the expression of the human or the mammalian IL-1Ra gene is regulated by a one component inflammation-inducible promoter, which is located upstream of a reading frame of the nucleic acid sequence encoding the human or the mammalian IL-1Ra and which is specifically activated by immune stimulatory substances into one or more joints of a subject in need of treatment by intra-articular injection, wherein the inflammation-inducible promoter is an NF-kB promoter, and wherein the promoter, the left and the right inverted terminal repeats, the adenoviral packaging signal and the non-viral, non-coding stuffer nucleic acid sequences have at least 90% sequence homology to the nucleic acid sequence of SEQ ID NO: 2 or SEQ ID NO: 3.

* * * * *